United States Patent
Love et al.

(10) Patent No.: US 9,326,511 B2
(45) Date of Patent: May 3, 2016

(54) METHODS OF INHIBITING MICROBIAL BIOFILMS

(75) Inventors: William Guy Love, Horsham (GB); William Rhys-Williams, Burgess Hill (GB)

(73) Assignee: Destiny Pharma Limited, Brighton (GB)

( * ) Notice: Subject to any disclaimer, the term of this patent is extended or adjusted under 35 U.S.C. 154(b) by 0 days.

(21) Appl. No.: 13/124,508

(22) PCT Filed: Oct. 23, 2009

(86) PCT No.: PCT/GB2009/002537
§ 371 (c)(1),
(2), (4) Date: Apr. 15, 2011

(87) PCT Pub. No.: WO2010/046663
PCT Pub. Date: Apr. 29, 2010

(65) Prior Publication Data
US 2011/0262511 A1    Oct. 27, 2011

Related U.S. Application Data

(60) Provisional application No. 61/193,054, filed on Oct. 24, 2008.

(51) Int. Cl.
| | | |
|---|---|---|
| *A01N 43/36* | (2006.01) | |
| *A01N 43/50* | (2006.01) | |
| *A01N 59/00* | (2006.01) | |
| *A01N 59/06* | (2006.01) | |
| *A01N 59/16* | (2006.01) | |
| *A01N 59/20* | (2006.01) | |
| *A61K 31/409* | (2006.01) | |

(52) U.S. Cl.
CPC .............. *A01N 43/36* (2013.01); *A01N 43/50* (2013.01); *A01N 59/00* (2013.01); *A01N 59/06* (2013.01); *A01N 59/16* (2013.01); *A01N 59/20* (2013.01); *A61K 31/409* (2013.01)

(58) Field of Classification Search
CPC ....... A01N 43/36; A01N 43/50; A01N 59/00; A01N 59/16; A01N 59/20; A01N 59/06; A61K 31/409
See application file for complete search history.

(56) References Cited

U.S. PATENT DOCUMENTS

| | | | |
|---|---|---|---|
| 2006/0020310 A1* | 1/2006 | Loebel et al. | 607/89 |
| 2006/0234959 A1* | 10/2006 | Biel | A61K 31/14 514/28 |
| 2011/0218139 A1 | 9/2011 | Robinson et al. | |

FOREIGN PATENT DOCUMENTS

| | | |
|---|---|---|
| GB | 2 415 372 A | 12/2005 |
| WO | 2004/056828 | 7/2004 |
| WO | WO 2004056828 A2 * | 7/2004 |
| WO | 2006/000765 | 1/2006 |
| WO | 2007/074340 | 7/2007 |

OTHER PUBLICATIONS

Andrews, J.M. "Determination of minimum inhibitory concentrations." J Antimicrob Chemother. Jul. 2001;48 Suppl 1:5-16.
Biavasco, F., et al. "In vitro antibacterial activity of LY333328, a new semisynthetic glycopeptide." Antimicrob Agents Chemother. Oct. 1997;41(10):2165-72.
Bruckner C., et al. "Novel and improved syntheses of 5,15-Diphenylporphyrin and its Dipyrrolic Prescursors." Journal of Porphyrins and Phthalocyanines. 1998;2:455-465.
Cassels, R., et al. "Occurrence of the regulatory nucleotides ppGpp and pppGpp following induction of the stringent response in staphylococci." J Bacteriol. Sep. 1995;177(17):5161-5.
Ceri, H., et al. "The Calgary Biofilm Device: new technology for rapid determination of antibiotic susceptibilities of bacterial biofilms." J Clin Microbiol. Jun. 1999;37(6):1771-6.
Chambrier, I., et al. "Porphyrin self-assembled monolayers and photodynamic oxidation or tryptophan." Journal of Porphyrins and Phthalocyanines. 2010;14:81-88.
Characklis, W.G., et al. "Influence of Fouling Biofilms on Heat Transfer." Heat Tran. Eng. 1981;3:23-37.
Collins, T.L., et al. "The effect of a cationic porphyrin on Pseudomonas aeruginosa biofilms." Curr Microbiol. Nov. 2010;61(5):411-6. Epub Apr. 6, 2010.
Costerton, J.W. "Cystic fibrosis pathogenesis and the role of biofilms in persistent infection." Trends Microbiol. Feb. 2001;9(2):50-2.
Critchley, I.A., et al. "Baseline study to determine in vitro activities of daptomycin against gram-positive pathogens isolated in the United States in 2000-2001." Antimicrob Agents Chemother. May 2003;47(5):1689-93.

(Continued)

*Primary Examiner* — Michael G Hartley
*Assistant Examiner* — Robert Cabral
(74) *Attorney, Agent, or Firm* — Robert C. Netter, Jr.; Dann, Dorfman, Herrell and Skillman

(57) ABSTRACT

The invention provides the use of a compound of formula (I), or metallated derivative thereof, for killing, inhibiting or preventing the growth of a microbial biofilm: wherein $X_1$, $X_2$, $X_3$, $X_4$, $Y_1$, $Y_2$, $Y_3$, $Y_4$ and $Z$ have meanings given in the description. The biofilm may be on a living or inert support. Preferably, the microorganisms are selected from the group consisting of bacteria and fungi.

18 Claims, 22 Drawing Sheets

(I)

(56) References Cited

OTHER PUBLICATIONS

Donlan, R.M., et al. "Biofilms: microbial life on surfaces." Emerg Infect Dis. Sep. 2002;8(9):881-90.
Farrell, D.J., et al. "In vitro activity of XF-73, a novel antibacterial agent, against antibiotic-sensitive and -resistant Gram-positive and Gram-negative bacterial species." Int J Antimicrob Agents. Jun. 2010;35(6):531-6. Epub Mar. 25, 2010.
Farrell, D.J., et al. "Investigation of the potential for mutational resistance to XF-73, retapamulin, mupirocin, fusidic acid, daptomycin, and vancomycin in methicillin-resistant *Staphylococcus aureus* isolates during a 55-passage study." Antimicrob Agents Chemother. Mar. 2011;55(3):1177-81. Epub Dec. 13, 2010.
Fuchs, P.C., et al. "In vitro bactericidal activity of daptomycin against staphylococci." J Antimicrob Chemother. Mar. 2002;49(3):467-70.
Guerra, H., et al. "The brucellae and their success as pathogens." Crit Rev Microbiol. 2007;33(4):325-31.
Hall-Stoodley, L., et al. "Bacterial biofilms: from the natural environment to infectious diseases." Nat Rev Microbiol. Feb. 2004;2(2):95-108.
Hassan, S.A., et al. "Activity of XF-70, a novel porphyrin antibacterial agent against biofilms of *Staphylococcus epidermis*." ECCMID London. 2012. Poster P1434.
Hassan, S.A., et al. "XF-73, a novel porphyrin with antibacterial activity against *Staphylococcus epidermis* irrespective of the growth state." ECCMID London. 2012. Poster P2173.
Hobbs, J.K., et al. "Consequences of daptomycin-mediated membrane damage in *Staphylococcus aureus*." J Antimicrob Chemother. Nov. 2008;62(5):1003-8. Epub Jul. 31, 2008.
Horsburgh, M.J., et al. "sigmaB modulates virulence determinant expression and stress resistance: characterization of a functional rsbU strain derived from *Staphylococcus aureus* 8325-4." J Bacteriol. Oct. 2002;184 (19):5457-67.
Hortuk, M.G., et al. "The novel antibacterial drug XF-70 is a potent inhibitor of *Staphylococcus aureus* infection of the burn wound." J Burn Care Res. May-Jun. 2010;31(3):462-9.
Kolter, R., et al. "The stationary phase of the bacterial life cycle." Annu Rev Microbiol. 1993;47:855-74.
Lauderdale, K.J., et al. "Interconnections between Sigma B, agr, and proteolytic activity in *Staphylococcus aureus* biofilm maturation." Infect Immun. Apr. 2009;77(4):1623-35. Epub Feb. 2, 2009.
Love, W.G., et al. "XF-73: A novel antimicrobial with Broad-Ranging Gram-Positive Antibacterial Activity." ECCMID Barcelona. 2008. Abstract, p. 559.
Lowry, O.H., et al. "Protein measurement with the Folin phenol reagent." J Biol Chem. Nov. 1951;193(1):265-75.
Maisch, T., et al. "Photodynamic effects of novel XF porphyrin derivatives on prokaryotic and eukaryotic cells." Antimicrob Agents Chemother. Apr. 2005;49(4):1542-52.
Maisch, T., et al. "Determination of the antibacterial efficacy of a new porphyrin-based photosensitizer against MRSA ex vivo." Photochem Photobiol Sci. May 2007;6(5):545-51. Epub Feb. 23, 2007.
Mascio, C.T., et al. "Bactericidal action of daptomycin against stationary-phase and nondividing *Staphylococcus aureus* cells." Antimicrob Agents Chemother. Dec. 2007;51(12):4255-60. Epub Oct. 8, 2007.
Mehta, et al. "Cholate-interspersed porphyrin-anthraquinone conjugates: Photonuclease activity of large sized, 'tweezer-like' molecules" J. Chem. Soc. Perkin. Trans. 1999;1:2177-2181.
Miller, K., et al. "XF-73: A new antimicrobial drug, active against biofilms and slow growing cultures of *Staphylococcus aureus*." (2008), ICAAC/IDSA Washington, Poster F1-3968.
Miller, K., et al. "Antistaphylococcal activity of the novel cephalosporin CB-181963 (CAB-175)." J Antimicrob Chemother. Apr. 2005;55(4):579-82. Epub Feb. 18, 2005.
Molina, A., et al. "High prevalence in cystic fibrosis patients of multiresistant hospital-acquired methicillin-resistant *Staphylococcus aureus* ST228-SCCmecl capable of biofilm formation." J Antimicrob Chemother. Nov. 2008;62 (5):961-7. Epub Jul. 21, 2008.
Mosmann, T. "Rapid colorimetic assay for cellular growth and survival: application to proliferation and cytotoxicity assays." Journal of Immunological Methods. 1983;65:55-63.
Nataro, J.P., et al. "Persistant bacterial infections: commensalism gone awry or adaptive niche?" in Persistant Bacterial Infections, J.P. Nataro, et al Eds. 2000;3-10.
Oliva, B., et al. "Biological properties of novel antistaphylococcal quinoline-indole agents." Antimicrob Agents Chemother. Feb. 2003;47(2):458-66.
Ooi, N., et al. "XF-70: A novel anti-staphylococcus drug active against biofilms and slow growing cultures." (2009), ICAAC San Francisco, Poster F1-837.
Ooi, N., et al. "XF-73, A novel antistaphylococcal membrane-active agent with rapid bactericidal activity." J Antimicrob Chemother. Oct. 2009;64(4):735-40. Epub Aug. 18, 2009.
Research on Microbial Biofilms (PA-03-047), National Heart Lung and Blood Institute 2002 <http://grants.nih.gov/grants/guide/pa-files/PA-03-047.html> (accessed on Mar. 30, 2012).
Somerville, G.A., et al. "*Staphylococcus aureus* aconitase inactivation unexpectedly inhibits post-exponential-phase growth and enhances stationary-phase survival." Infect Immun. Nov. 2002;70(11):6373-82.
Stewart, P.S., et al. "Antibiotic resistance of bacteria in biofilms." Lancet. Jul. 14, 2001;358(9276):135-8.
Toney, J.H. "Biofilms—a neglected antibacterial target?" Curr Opin Investig Drugs. Aug. 2007;8(8):598-9.
Traxler, M.F., et al. "The global, ppGpp-mediated stringent response to amino acid starvation in *Escherichia coli*." Mol Microbiol. Jun. 2008;68(5):1128-48. Epub Apr. 22, 2008.
Vaudaux, P., et al. "*Staphylococcus aureus* small colony variants: difficult to diagnose and difficult to treat." Clin Infect Dis. Oct. 15, 2006;43(8):968-70. Epub Sep. 8, 2006.
Vaudaux, P., et al. "Extracellular and intracellular bactericidal activities of XF-70 against small-colony variant hemB mutants of meticillin-susceptible and meticillin-resistant *Staphylococcus aureus*." Int J Antimicrob Agents. Jun. 2011;37 (6):576-9. Epub Mar. 16, 2011.
Wiehe, A., et al. "Hydrophilicity vs hydrophobicity—varying the amphiphilic structure of porphyrins related to the photosensitizer m-THPC." Journal of Porphyrins and Phthalocyanines. 2001;5:758-761.
Williams, I., et al. "The effects of adherence to silicone surfaces on antibiotic susceptibility in *Staphylococcus aureus*." Microbiology. Jul. 1997;143 ( Pt 7):2407-13.
Ooi, N., et al. "XF-70 and XF-73, novel antibacterial agents active against slow-growing and non-dividing cultures of *Staphylococcus aureus* including biofilms." J Antimicrob Chemother. Adv. Access. Nov. 4, 2009;1-7.

* cited by examiner

Compound 1

METHODS OF INHIBITING MICROBIAL BIOFILMS

This is a national stage application of PCT/GB2009/002537, filed on Oct. 23, 2009, which claims priority to U.S. Provisional Application 61/193,054, filed on Oct. 24, 2008. The entire disclosure of each of the foregoing applications is incorporated by reference herein.

FIELD

The present invention relates to new uses of porphyrin compounds and, in particular, the use of such compounds in the killing, inhibition or prevention of microbial biofilms (in medicine as well as in domestic, commercial and industrial environments).

BACKGROUND

The formation of biofilms is a universal bacterial survival strategy. Biofilms occur on both inert and living supports, in natural environments and in industrial installations.

A biofilm is a structured community of microorganisms encapsulated within a self-developed polymeric matrix and adherent to a living or inert surface. Biofilms are also often characterized by surface attachment, structural heterogeneity, genetic diversity, complex community interactions, and an extracellular matrix of polymeric substances.

Single-celled organisms generally exhibit two distinct modes of behavior. The first is the familiar free floating, or planktonic, form in which single cells float or swim independently in some liquid medium. The second is an attached state in which cells are closely packed and firmly attached to each other and usually form a solid surface. A change in behavior is triggered by many factors, including quorum sensing, as well as other mechanisms that vary between species. When a cell switches modes, it undergoes a phenotypic shift in behavior in which large suites of genes are up- and down-regulated.

Formation

Formation of a biofilm begins with the attachment of free-floating microorganisms to a surface. These first colonists adhere to the surface initially through weak, reversible van der Waals forces. If the colonists are not immediately separated from the surface, they can anchor themselves more permanently using cell adhesion structures such as pili.

The first colonists facilitate the arrival of other cells by providing more diverse adhesion sites and beginning to build the matrix that holds the biofilm together. Some species are not able to attach to a surface on their own but are often able to anchor themselves to the matrix or directly to earlier colonists. It is during this colonization that the cells are able to communicate via quorum sensing. Once colonization has begun, the biofilm grows through a combination of cell division and recruitment. The final stage of biofilm formation is known as development, and is the stage in which the biofilm is established and may only change in shape and size. This development of biofilm allows for the cells to become more antibiotic resistant. Bacterial biofilms are thought to be refractive to antibiotic action for at least two reasons; the biofilm forms a physical barrier preventing antibiotic penetration to the bacteria, and secondly the bacteria within biofilms tend to grow more slowly, hence providing a lower metabolic profile for antibiotics to target.

Properties

Biofilms are usually found on solid substrates submerged in or exposed to some aqueous solution, although they can form as floating mats on liquid surfaces and also on the surface of leaves, particularly in high humidity climates. Given sufficient resources for growth, a biofilm will quickly grow to be macroscopic. Biofilms can contain many different types of microorganism, e.g. bacteria, archaea, protozoa, fungi and algae; each group performing specialized metabolic functions. However, some organisms will form mono-species films under certain conditions.

Biofilms appear able to defend themselves against disinfectants and antibiotics, phagocytes and the human immune system.

Extracellular Matrix

The biofilm is held together and protected by a matrix of excreted polymeric compounds called EPS. EPS is an abbreviation for either extracellular polymeric substance or exopolysaccharide. This matrix protects the cells within it and facilitates communication among them through biochemical signals. Some biofilms have been found to contain water channels that help distribute nutrients and signaling molecules. This matrix is strong enough that under certain conditions, biofilms can become fossilized.

Bacteria living in a biofilm usually have significantly different properties from free-floating bacteria of the same species, as the dense and protected environment of the film allows them to cooperate and interact in various ways. One benefit of this environment is increased resistance to detergents and antibiotics, as the dense extracellular matrix and the outer layer of cells protect the interior of the community. In some cases antibiotic resistance can be increased 1000 fold (see Stewart P, Costerton J, 2001, *Lancet* 358 (9276): 135-8).

EXAMPLES

Biofilms are ubiquitous. Nearly every species of microorganism, not only bacteria and archaea, have mechanisms by which they can adhere to surfaces and to each other.

Biofilms can be found on rocks and pebbles at the bottom of most streams or rivers and often form on the surface of stagnant pools of water. In fact, biofilms are important components of food chains in rivers and streams and are grazed by the aquatic invertebrates upon which many fish feed.

Biofilms grow in hot, acidic pools in Yellowstone National Park (USA) and on glaciers in Antarctica.

Biofilms can grow in showers very easily since they provide a moist and warm environment for the biofilm to thrive.

Biofilms can develop on the interiors of pipes leading to clogging and corrosion.

Biofilms on floors and counters can make sanitation difficult in food preparation areas. Biofilms in cooling water systems are known to reduce heat transfer (see W. G. Characklis, et al., 1981, *Heat Trans. Eng.* 3:23-37

Bacterial adhesion to boat hulls serves as the foundation for biofouling of seagoing vessels. Once a film of bacteria forms, it is easier for other marine organisms such as barnacles to attach. Such fouling can inhibit vessel speed by up to 20%, making voyages longer and requiring additional fuel. Time in dry dock for refitting and repainting reduces the productivity of shipping assets, and the useful life of ships is also reduced due to corrosion and mechanical removal (scraping) of marine organisms from ships' hulls.

Biofilms can also be harnessed for constructive purposes. For example, many sewage treatment plants include a treatment stage in which waste water passes over biofilms grown on filters, which extract and digest organic compounds. In such biofilms, bacteria are mainly responsible for removal of organic matter (BOD); whilst protozoa and rotifers are mainly responsible for removal of suspended solids (SS), including pathogens and other microorganisms. Slow sand filters rely on biofilm development in the same way to filter surface water from lake, spring or river sources for drinking purposes. What we regard as clean water is a waste material to these microcellular organisms since they are unable to extract any further nutrition from the purified water.

Biofilms can help eliminate petroleum oil from contaminated oceans or marine systems. The oil is eliminated by the hydrocarbon-degrading activities of microbial communities, in particular by a remarkable recently discovered group of specialists, the so-called hydrocarbonoclastic bacteria (HCB).

Biofilms are also present on the teeth of most animals as dental plaque, where they may become responsible for tooth decay and gum disease.

Biofilms are found on the surface of and inside plants. They can both contribute to crop disease or, as in the case of nitrogen fixing *Rhizobium* on roots, exist symbiotically with the plant [6]. Examples of crop diseases related to biofilms include Citrus Canker, Pierce's Disease of grapes, and Bacterial Spot of plants such as peppers and tomatoes.

Biofilms and Infectious Diseases

Biofilms have been found to be involved in a wide variety of microbial infections in the body, by one estimate 80% of all infections (see "Research on microbial biofilms (PA-03-047)", NIH, National Heart, Lung, and Blood Institute, Dec. 20, 2002). Infectious processes in which biofilms have been implicated include common problems such as urinary tract infections, catheter infections, middle-ear infections, formation of dental plaque, gingivitis, coating contact lenses, and less common but more lethal processes such as endocarditis, infections in cystic fibrosis, and infections of permanent indwelling devices such as joint prostheses and heart valves.

It has recently been shown that biofilms are present on the removed tissue of 80% of patients undergoing surgery for chronic sinusitis. The patients with biofilms were shown to have been denuded of cilia and goblet cells, unlike the controls without biofilms who had normal cilia and goblet cell morphology. Biofilms were also found on samples from two of 10 healthy controls mentioned. The species of bacteria from interoperative cultures did not correspond to the bacteria species in the biofilm on the respective patient's tissue. In other words, the cultures were negative though the bacteria were present.

*Pseudomonas aeruginosa* Biofilms

The achievements of medical care in industrialised societies are markedly impaired due to chronic opportunistic infections that have become increasingly apparent in immunocompromised patients and the aging population. Chronic infections remain a major challenge for the medical profession and are of great economic relevance because traditional antibiotic therapy is usually not sufficient to eradicate these infections. One major reason for persistence seems to be the capability of the bacteria to grow within biofilms that protects them from adverse environmental factors. *Pseudomonas aeruginosa* is not only an important opportunistic pathogen and causative agent of emerging nosocomial infections but can also be considered a model organism for the study of diverse bacterial mechanisms that contribute to bacterial persistence. In this context the elucidation of the molecular mechanisms responsible for the switch from planctonic growth to a biofilm phenotype and the role of inter-bacterial communication in persistent disease should provide new insights in *P. aeruginosa* pathogenicity, contribute to a better clinical management of chronically infected patients and should lead to the identification of new drug targets for the development of alternative anti-infective treatment strategies.

Dental Plaque

Dental plaque is the material that adheres to the teeth and consists of bacterial cells (mainly *Streptococcus mutans* and *Streptococcus sanguis*), salivary polymers and bacterial extracellular products. Plaque is a biofilm on the surfaces of the teeth. This accumulation of microorganisms subjects the teeth and gingival tissues to high concentrations of bacterial metabolites which results in dental disease.

Legionellosis

*Legionella* bacteria are known to grow under certain conditions in biofilms, in which they are protected against disinfectants. Workers in cooling towers, persons working in air conditioned rooms and people taking a shower may be exposed to *Legionella* by inhaling where the systems are not well constructed and designed, and maintained properly.

Interestingly, microorganisms such as bacteria that attach to a surface and grow as a biofilm are less vulnerable to conventional antibiotic treatments. Reduced antibiotic susceptibility contributes to the persistence of biofilm infections such as those associated with implanted devices. The protective mechanisms at work in biofilms appear to be distinct from those that are responsible for conventional antibiotic resistance. In biofilms, poor antibiotic penetration, nutrient limitation, slow growth, adaptive stress responses, and formation of persister cells are hypothesized to constitute a multi-layered defence.

Furthermore, biofilm cultures are typically highly refractory to eradication with chemotherapy, without developing genotypic resistance. Consequently, the number of therapeutic options is limited and the development of novel antimicrobial agents with antibiofilm activity is increasingly important.

Hence, there is a need for new methods of killing, inhibiting or preventing the growth of a microbial biofilms (both in medical and non-medical environments).

SUMMARY OF THE INVENTION

According to a first aspect of the invention, there is provided use of a compound of formula I for killing, inhibiting or preventing the growth of a microbial biofilm:

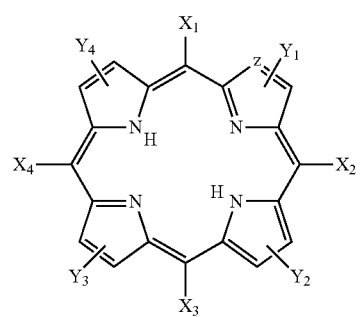

wherein:
$X_1$, $X_2$, $X_3$ and $X_4$ independently represent (i.e. are the same or different) a hydrogen atom, a lipophilic moiety, a phenyl group, a lower alkyl, alkaryl or aralkyl group, or a cationic group of the following formula;

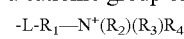

wherein:

L is a linking moiety or is absent;

$R_1$ represents lower alkylene, lower alkenylene or lower alkynylene, which is optionally substituted by one or more substituents selected from lower alkyl, lower alkylene (optionally interrupted with oxygen), fluoro, $OR_5$, $C(O)R_6$, $C(O)OR_7$, $C(O)NR_8R_9$, $NR_{10}R_{11}$ and $N^+R_{12}R_{13}R_{14}$; and $R_2$, $R_3$ and $R_4$ independently represent (i.e. are the same or different) H, aryl, lower alkyl, lower alkenyl or lower alkynyl, the latter three of which are optionally substituted by one or more substituents selected from lower alkyl, lower alkylene (optionally interrupted with oxygen), aryl, $OR_5$, $C(O)R_6$, $C(O)OR_7$, $C(O)NR_8$, $R_9$, $NR_{10}R_{11}$ and $N^+R_{12}R_{13}R_{14}$ Z is —CH or N;

$Y_1$, $Y_2$, $Y_3$ and $Y_4$ are absent or independently represent aryl, lower alkyl, lower alkenyl or lower alkynyl, the latter three of which are optionally substituted by one or more substituents selected from lower alkyl, lower alkylene (optionally interrupted with oxygen), aryl, $OR_5$, $C(O)R_6$, $C(O)OR_7$, $C(O)NR_8$, $R_9$, $NR_{10}R_{11}$, $N^+R_{12}R_{13}R_{14}$, or, taken in conjunction with the pyrrole ring to which they attach, may form a cyclic group; and $R_5$, $R_6$, $R_7$, $R_8$, $R_9$, $R_{10}$, $R_{11}$, $R_{12}$, $R_{13}$ and $R_{14}$ independently represent H or lower alkyl provided that at least one of $X_1$, $X_2$, $X_3$ and $X_4$ is a cationic group as defined above and at least one of $X_1$, $X_2$, $X_3$ and $X_4$ is a hydrogen atom, a phenyl group, a lipophilic moiety, or a lower alkyl, alkaryl or aralkyl group.

By "biofilm" we include microbial (e.g. bacterial, fungal, algal) communities, typically enveloped by an extracellular matrix produced by the microbial cells, which can adhere to the interface of a liquid and a surface (for example, on a mucosal membrane within the body, any host tissue or organ, or on the surface of a permanent or semi-permanent implanted medical device (e.g. venous catheter)).

The term "lower alkyl" is intended to include linear or branched, cyclic or acyclic, $C_1$-$C_{20}$ alkyl which may be interrupted by oxygen (preferably no more than five oxygen atoms are present in each alkyl chain). Lower alkyl groups which $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ may represent include $C_1$-$C_{18}$ alkyl, $C_1$-$C_{16}$ alkyl, $C_1$-$C_{14}$ alkyl, $C_1$-$C_{12}$ alkyl, $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_6$ alkyl, $C_1$-$C_4$ alkyl, $C_1$-$C_3$ alkyl and $C_1$-$C_2$ alkyl. Preferred lower alkyl groups which $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ may represent include $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$ and $C_{16}$ alkyl.

Thus, any one or more of $N^+R_2R_3R_4$ and/or $N^+R_{12}R_{13}R_{14}$ may represent cyclic amine/ammonium groups, for example:

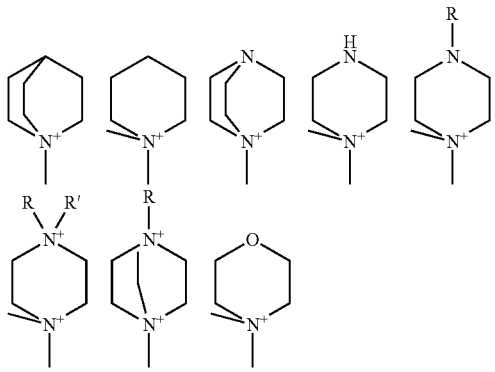

(wherein the group is attached to the compound by the undefined bond from the $N^+$ atom, as shown at the bottom of the above structures)

It will be appreciated that the cyclic amine/ammonium groups may also comprise fewer or greater than six members, for example such groups may comprise 4-, 5-, 7-, 8-, 9- or 10-membered rings.

The term "lower alkylene" is to be construed accordingly.

The terms "lower alkenyl" and "lower alkynyl" are intended to include linear or branched, cyclic or acyclic, $C_2$-$C_{20}$ alkenyl and alkynyl, respectively, each of which may be interrupted by oxygen (preferably no more than five oxygen atoms are present in each alkenyl or alkynyl chain).

The term "lower alkenyl" also includes both the cis and trans geometric isomers. Lower alkenyl groups which $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ may represent include $C_2$-$C_{18}$ alkenyl, $C_2$-$C_{17}$ alkenyl, $C_2$-$C_{16}$ alkenyl, $C_2$-$C_{14}$ alkenyl, $C_2$-$C_{12}$ alkenyl, $C_2$-$C_{10}$ alkenyl, $C_2$-$C_8$ alkenyl, $C_2$-$C_7$ alkenyl, $C_2$-$C_6$ alkenyl, $C_2$-$C_5$ alkenyl, $C_2$-$C_4$ alkenyl, $C_2$-$C_3$ alkenyl and $C_3$-$C_4$ alkenyl. Preferred lower alkenyl groups which $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ may represent include $C_2$, $C_3$, $C_4$, $C_5$, $C_6$, $C_7$, $C_8$, $C_9$, $C_{10}$, $C_{11}$, $C_{12}$, $C_{13}$ and $C_{14}$ alkenyl.

The term "lower alkenylene" is to be construed accordingly.

"Lower alkynyl" groups which $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ may represent include $C_2$-$C_{18}$ alkynyl, $C_2$-$C_{16}$ alkynyl, $C_2$-$C_{14}$ alkynyl, $C_2$-$C_{12}$ alkynyl, $C_2$-$C_{10}$ alkynyl, $C_2$-$C_9$ alkynyl, $C_2$-$C_8$ alkynyl, $C_2$-$C_7$ alkynyl, $C_2$-$C_6$ alkynyl, $C_2$-$C_5$ alkynyl, $C_2$-$C_4$ alkynyl, $C_2$-$C_3$ alkynyl and $C_3$-$C_4$ alkynyl. Preferred lower alkynyl groups which $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ may represent include $C_2$, $C_3$, $C_4$, $C_5$, $C_6$, $C_7$, $C_8$, $C_9$, $C_{10}$, $C_{11}$, $C_{12}$, $C_{13}$ and $C_{14}$ alkynyl.

The term "lower alkynylene" is to be construed accordingly.

The term "aryl" includes six to ten-membered carbocyclic aromatic groups, such as phenyl and naphthyl, which groups are optionally substituted by one or more substituents selected from fluoro, cyano, nitro, lower alkyl (i.e. alkaryl), $OR_5$, $C(O)R_6$, $C(O)OR_7$, $C(O)NR_8R_9$ and $NR_{10}R_{11}$.

The term "aralkyl" includes aryl groups joined to the porphyrin ring via a lower alkyl group.

A second aspect of the invention provides use of a compound of formula II for killing, inhibiting or preventing the growth of a microbial biofilm:

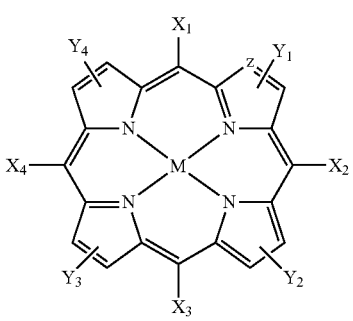

II wherein M is a metallic element or a metalloid element and $X_1$, $X_2$, $X_3$, $X_4$, $Y_1$, $Y_2$, $Y_3$, $Y_4$ and Z are as defined above.

The term "metallic element" is intended to include a divalent or trivalent metallic element. Preferably, the metallic element is diamagnetic. Alternatively, the metallic element may be paramagnetic.

More preferably, the metallic element is selected from Zn(II), Cu(II), La(III), Lu(III), Y(III), In(III) Cd(II), Mg(II), Al(III), Ru, Ni(II), Mn(III), Fe(III) and Pd(II). Most preferably, the metallic element is Cu(II) or Fe(III).

The term "metalloid" is intended to include an element having physical and chemical properties, such as the ability to conduct electricity, that are intermediate to those of both metals and non-metals. The term "metalloid element" includes silicon (Si) and germanium (Ge) atoms which are optionally substituted with one or more ligands.

It will be appreciated that the terms metallic element and metalloid element include a metal element or a metalloid element having a positive oxidation state, all of which may be substituted by one or more ligands selected from fluoro, OH, $OR_{15}$ wherein $R_{15}$ is lower alkyl, lower alkenyl, lower alkynyl, aralkyl, aryl or alkaryl as defined above (wherein aryl and alkaryl are mono-substituted).

The compounds of formulae I and II comprise at least one cationic group. Thus, the compounds of the invention may carry a net positive charge, for example a charge of +1, +2, +3, +4, +5, +6 or more. In a preferred embodiment, the compounds carry a net charge of less than +4, for example +1, +2 or +3. In a particularly preferred embodiment, the compounds carry a net charge of +2.

It will be appreciated by persons skilled in the art that compounds of formulae I and II may be counterbalanced by counter-anions. Exemplary counter-anions include, but are not limited to, halides (e.g. fluoride, chloride and bromide), sulfates (e.g. decylsulfate), nitrates, perchlorates, sulfonates (e.g. methane sulfonate) and trifluoroacetate. Other suitable counter-anions will be well known to persons skilled in the art. Thus, pharmaceutically, and/or veterinarily, acceptable derivatives of the compounds of formulae I and II, such as salts and solvates, are also included within the scope of the invention. Salts which may be mentioned include: acid addition salts, for example, salts formed with inorganic acids such as hydrochloric, hydrobromic, sulfuric and phosphoric acid, with carboxylic acids or with organo-sulfonic acids; base addition salts; metal salts formed with bases, for example, the sodium and potassium salts.

It will be further appreciated by skilled persons that the compounds of formula I may exhibit tautomerism. All tautomeric forms and mixtures thereof are included within the scope of the invention.

Compounds of formulae I and II may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively, the desired optical isomers may be made by reaction of the appropriate optically active starting materials under conditions which will not cause racemisation or epimerisation, or by derivatisation, for example with a homochiral acid followed by separation of the diastereomeric esters by conventional means (e.g. HPLC, chromatography over silica). All stereoisomers are included within the scope of the invention.

In a preferred embodiment of the first and second aspects of the invention, Z is —CH.

A characterising feature of the first and second aspects of the invention is that at least one of substituent groups $X_1$, $X_2$, $X_3$ and $X_4$ is a quaternary ammonium cationic group of the formula $-L-R_1-N^+(R_2)(R_3)R_4$, as defined above. Preferably, none of $X_1$, $X_2$, $X_3$ and $X_4$ is an anilinium or a pyridinium cationic group.

In a preferred embodiment, $R_1$ is an unsubstituted lower alkylene, lower alkenylene or lower alkynylene group.

Advantageously, $R_1$ is a straight-chain lower alkylene group of formula:

Preferably, 'm' is an integer between 1 and 20. More preferably, 'm' is an integer between 1 and 10, for example between 1 and 6, between 1 and 5, between 1 and 4 or between 1 and 3. Preferred straight-chain lower alkylene groups which $R_1$ may represent include groups of the above formula wherein m is 2, 3, 4, 5, 6, 7, 8, 9 or 10. Most preferably, 'm' is 2 or 3.

The remaining three substituent groups of the quaternary ammonium moiety, i.e. $R_2$, $R_3$ and $R_4$, may be the same or different and are selected from H, lower alkyl, lower alkenyl or lower alkynyl, the latter three of which are optionally substituted by one or more substituents selected from lower alkyl, $OR_5$, $C(O)R_6$, $C(O)OR_7$, $C(O)NR_8$, $R_9$, $NR_{10}R_{11}$ and $N^+R_{12}R_{13}R_{14}$.

In a preferred embodiment, $R_2$, $R_3$ and/or $R_4$ are lower alkyl, lower alkenyl or lower alkynyl group.

Preferably, $R_2$, $R_3$ and/or $R_4$ are unsubstituted lower alkyl groups.

Optionally, at least one of $R_2$, $R_3$ and $R_4$ is an alkyl group which is substituted with a primary, secondary or tertiary amine group or a quaternary ammonium group.

In a preferred embodiment of the first and second aspects of the invention, $R_1$ is —$(CH_2)_3$—, $R_2$ and $R_3$ are $CH_3$ and $R_4$ is —$(CH_2)_3$—$N(CH_3)_2$.

In an alternative preferred embodiment of the first and second aspects of the invention, $R_1$ is —$(CH_2)_3$—, and $R_2$, $R_3$ and $R_4$ are each $CH_3$.

In a further alternative preferred embodiment of the first and second aspects of the invention, $R_1$ is —$(CH_2)_3$—, and $R_2$, $R_3$ and $R_4$ are each $C_2H_5$.

Advantageously, at least one of $X_1$, $X_2$, $X_3$ and $X_4$ is a cationic group as defined above and at least one of $X_1$, $X_2$, $X_3$ and $X_4$ is a hydrogen atom.

Preferably, each of $X_1$, $X_2$, $X_3$ and $X_4$ is a hydrogen atom or a cationic group as defined above.

Conveniently, the pK values of any primary, secondary or tertiary amine groups, if present in the compounds of the invention, is greater than 8 to ensure that the group is protonated when in a physiological environment.

The quaternary ammonium cationic group is optionally joined to the porphyrin ring via a linking moiety, L.

Preferred linking moieties, L, include phenoxy, phenylene, sulfonyl amido, aminosulfonyl, sulfonylimino, phenylsulfonylamido, phenyl-aminosulfonyl, urea, urethane and carbamate linking moieties.

In a preferred embodiment, the quaternary ammonium cationic group is joined to the porphyrin ring via a phenoxy linker.

Thus, $X_1$, $X_2$, $X_3$ and/or $X_4$ may have the following formula:

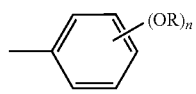

wherein R is $R_1$—$N^+(R_2)(R_3)R_4$, as defined above, and 'n' is an integer between 1 and 3 (and wherein the group is attached to the porphyrin ring via the free bond on the left).

In an alternative preferred embodiment, the quaternary ammonium cationic group is joined to the porphyrin ring via a phenylene linker.

Thus, $X_1$, $X_2$, $X_3$ and/or $X_4$ may have the following formula:

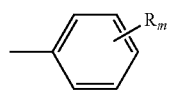

wherein R is $R_1-N^+(R_2)(R_3)R_4$, as defined above, and 'm' is an integer between 1 and 3 (and wherein the group is attached to the porphyrin ring via the free bond on the left).

Preferably, 'm' is 2, and most preferably 1.

In an alternative preferred embodiment, $X_1$, $X_2$, $X_3$ and/or $X_4$ may have the following formula:

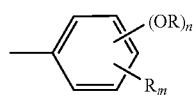

wherein R is $R_1-N^+(R_2)(R_3)R_4$, 'n' and 'm' are as defined above, and 'n+m' is between 1 and 3 (and wherein the group is attached to the porphyrin ring via the free bond on the left).

Advantageously, L comprises a benzene ring (e.g. phenoxy, phenylene, phenylsulfonylamido or phenylamino-sulfonyl) mono-substituted at the para-position relative to the benzene ring position at which the porphyrin macrocycle is attached. Alternatively, L may be mono- or di-substituted at meta- or ortho-positions relative to the benzene ring positions at which the porphyrin macrocycle is attached. L may also be both para- and ortho-substituted.

In an alternative preferred embodiment, the quaternary ammonium cationic group is joined directly to the porphyrin ring, i.e. L is absent.

In a preferred embodiment of the first and second aspects of the invention, the compound comprises two cationic groups, as defined above, on opposite sides of the porphyrin ring, i.e. at ring positions 5 and 15 or ring positions 10 and 20. For example, $X_1$ and $X_3$ may be a hydrogen atom, a lipophilic moiety, a phenyl group, a lower alkyl, alkaryl or aralkyl group, and $X_2$ and $X_4$ may be cationic groups, or vice versa. Preferably, $X_1$ and $X_3$ are both a hydrogen atom and $X_2$ and $X_4$ are both a cationic group, or vice versa.

Alternatively, the compound may comprise two cationic groups, as defined above, on neighbouring positions of the porphyrin ring, i.e. at ring positions 5 and 10, or ring positions 10 and 15, or ring positions 15 and 20 or ring positions 20 and 5. For example, $X_1$ and $X_2$ may be hydrogen and $X_3$ and $X_4$ may be cationic groups, or $X_2$ and $X_3$ may be hydrogen and $X_4$ and $X_1$ may be cationic groups, etc.

It will be appreciated by persons skilled in the art that additional isomeric structural possibilities arise when Z represents nitrogen. Such possibilities are included within the scope of the present invention.

In a further preferred embodiment of the first and second aspects of the invention, the compound is substituted on one or more of its constituent pyrrole rings. Thus, $Y_1$, $Y_2$, $Y_3$ and $Y_4$ may be absent or independently represent aryl, lower alkyl, lower alkenyl or lower alkynyl, the latter three of which are optionally substituted by one or more substituents selected from lower alkyl, lower alkylene (optionally interrupted with oxygen), aryl, $OR_5$, $C(O)R_6$, $C(O)OR_7$, $C(O)$ $NR_8$, $R_9$, $NR_{10}R_{11}$ and $N^+R_{12}R_{13}R_{14}$. It will be appreciated by skilled persons that $Y_1$, $Y_2$, $Y_3$ and/or $Y_4$ may comprise cyclic groups, which may be saturated or aromatic. For example, one or more of the pyrrole rings may be substituted to form an iso-indole group, i.e. $Y_1$, $Y_2$, $Y_3$ and/or $Y_4$ together with the pyrrole ring to which they are attached may be cyclic.

In an alternative preferred embodiment of the first and second aspects of the invention, $Y_1$, $Y_2$, $Y_3$ and $Y_4$ are absent. Thus, the porphyrin ring is preferably substituted only at one or more of positions 5, 10, 15 or 20.

In a further preferred embodiment of the first and second aspects of the invention, at least one of $X_1$, $X_2$, $X_3$ and $X_4$ is or comprises a lipophilic moiety.

By 'lipophilic moiety' we include moieties having a partition coefficient between 1-n-octanol and water expressed as log P of greater than 1.0 at physiological pH and 25° C.

Conveniently, the lipophilic moiety is a saturated, straight-chain alkyl group of formula $-(CH_2)_pCH_3$, or an equivalent alkylene group of formula $-(CH_2)_p-$, wherein 'p' is an integer between 1 and 22, for example between 1 and 18. Preferably, 'p' is between 1 and 18, more preferably between 2 and 16, between 4 and 16, between 6 and 18, between 8 and 16 or between 4 and 12. Most preferably, 'p' is between 10 and 12.

It will be appreciated that $X_1$, $X_2$, $X_3$ and/or $X_4$ may be a cationic group, as defined above, which also comprises a lipophilic moiety.

In an alternative preferred embodiment of the first and second aspects of the invention, none of $X_1$, $X_2$, $X_3$ and $X_4$ is a lipophilic moiety.

Advantageously, the compounds used in the first and second aspects of the invention are soluble in water. Preferably, the compounds may be dissolved in water to a concentration of at least 5 μg/l, for example at least 10 μg/l, 15 μg/l or 20 μg/l. More preferably, the compounds may be dissolved in water to a concentration of at least 100 μg/l, for example 200 μg/l, 300 μg/l, 400 μg/l, 500 μg/l, 1 mg/ml, 5 mg/ml, 10 mg/ml, 20 mg/ml, 50 mg/ml or 100 mg/ml.

Conveniently, the compounds used in the first and second aspects of the invention exhibit selective toxicity to microbial agents. By 'selective' we mean the compound is preferentially toxic to one or more microorganisms (such as bacteria, mycoplasmas, yeasts, fungi and/or viruses) compared to mammalian, e.g. human, host cells. Preferably, the toxicity of the compound to a target microorganism is at least two-fold greater than the toxicity of that compound to mammalian cells, more preferably at least three-fold, at least four-fold, at least five-fold, at least six-fold, at least eight-fold, at least ten-fold, at least fifteen-fold or at least twenty fold. Most preferably, the compound of the invention is substantially non-toxic to mammalian cells.

In this way, when the compounds are used to treat bacterial infections, for example, dosing regimes can be selected such that bacterial cells are destroyed with minimal damage to healthy host tissue. Thus, the compounds for use in the first and second aspects of the invention preferably exhibit a 'therapeutic window'.

In a preferred embodiment, the compound is toxic to the target microorganism (e.g. bacterial cells) at low doses. Preferably, the compound is toxic to the target microorganism at a concentration of less than 10 μM, for example less than 1 μM, less than 0.1 μM, less than 0.01 μM, less than 0.005 μM or less than 0.001 μM (see Example B).

Preferred compounds for use in the first and second aspects of the invention include the following:

(a) 5,15-bis-(4-{3-[(3-Dimethylamino-propyl)-dimethyl-ammonio]-propyloxy}-phenyl)-porphyrin ("Compound 8")

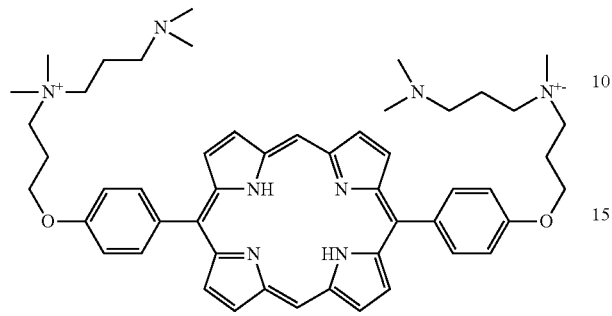

Preferably, this compound is provided as a dichloride or tetrachloride salt.

(b) 5,15-bis-[4-(3-Triethylammonio-propyloxy)-phenyl]-porphyrin ("Compound 9");

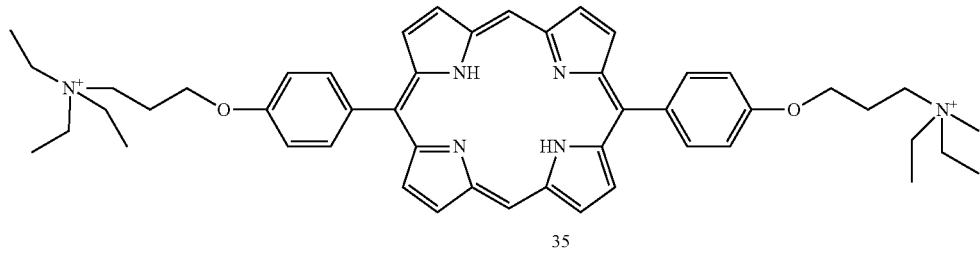

Preferably, this compound is provided as a dichloride salt.

(c) 5,15-bis-[3-(3-Trimethylammonio-propyloxy)-phenyl]-porphyrin (also referred to herein as "Compound 12" or "XF-70");

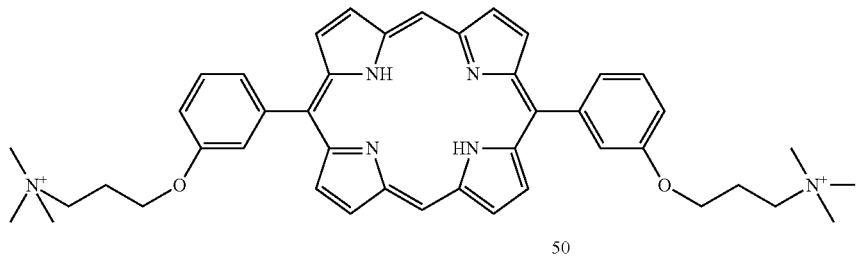

Preferably, this compound is provided as a dichloride salt.

(d) 5,15-bis-[4-(3-Trimethylammonio-propyloxy)-phenyl]-porphyrin (also referred to herein as "Compound 10" or "XF-73");

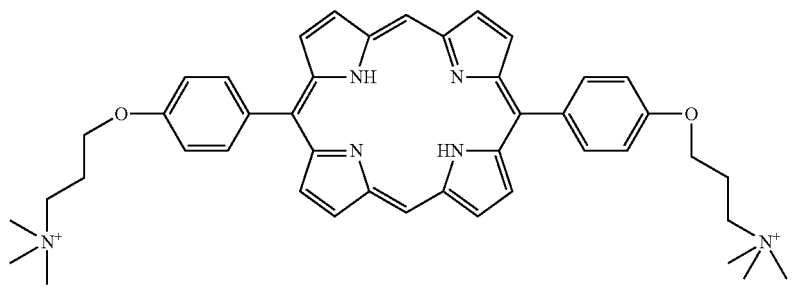

Preferably, this compound is provided as a dichloride salt.

(e) 5-[3,5-bis-(3-Trimethylammonio-propyloxy)-phenyl]-15-undecyl-porphyrin ("Compound 6");

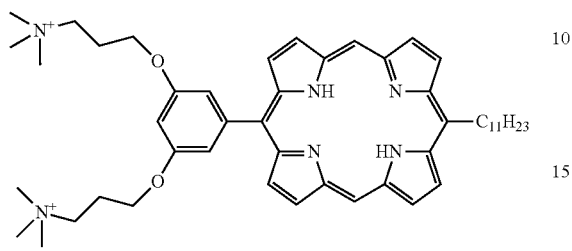

Preferably, this compound is provided as a dichloride salt.

(f) 5-{4-[3-Dimethyl-(3-dimethylaminopropyl)-ammonio-propyloxy]phenyl}-15-(4-dodecyloxy-phenyl)-porphyrin ("Compound 23");

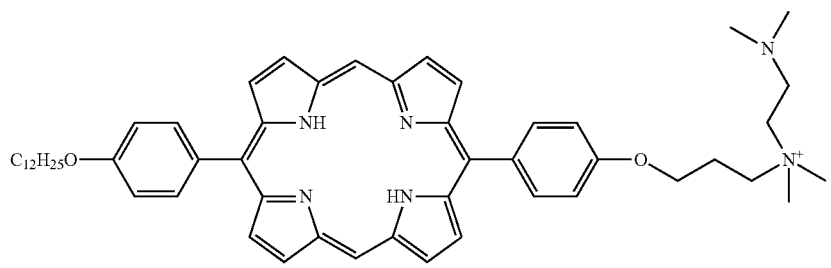

Preferably, this compound is provided as a chloride or dichloride salt.

(g) 3-[({3-[(3-{4-[15-(4-Dodecyloxy-phenyl)-porphyrin-5-yl]-phenoxy}-propyl)-dimethyl-ammonio]-propyl}-dimethyl-ammonio)-propyl]-trimethyl-ammonium ("Compound 25");

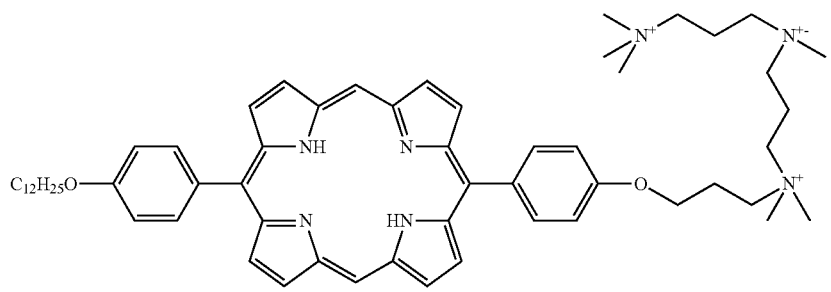

Preferably, this compound is provided as a trichloride salt.

(h) 5,15-bis-[3-(3-Trimethylammmonio-propyloxy)-phenyl]-10-undecyl-porphyrin ("Compound 28");

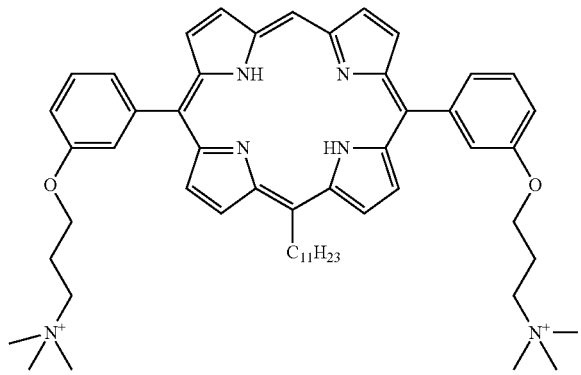

Preferably, this compound is provided as a dichloride salt.

(i) 5-{-4-[3-Dimethyl-(3-trimethylammonio-propyl)-ammonio-propyloxy]-phenyl}-15-(4-dodecyloxy-phenyl)-porphyrin ("Compound 31"); and

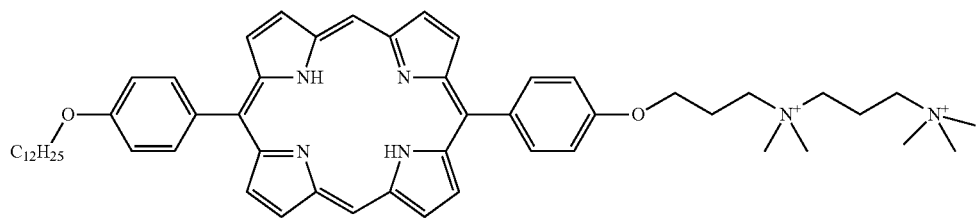

Preferably, this compound is provided as a dichloride salt.

(j) 5-[4-(3-Dimethyldecyl-ammoniopropyloxy)-phenyl]-15-{-4-[3-dimethyl-(3-dimethylaminopropyl)-ammoniopropyloxy]-phenyl}-porphyrin ("Compound 32")

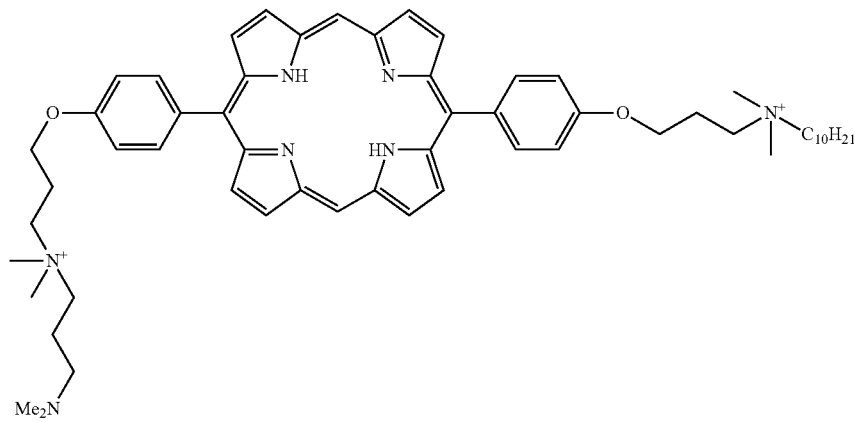

Preferably, this compound is provided as a dichloride salt.

In a particularly preferred embodiment, the compound is the dichloride salt of Compound 10 or Compound 12 above.

It will be appreciated that the above compounds may alternatively be in a metallated form, i.e. they may comprise a chelated metallic element or metalloid element within the porphyrin ring.

Preferred chelated metallic elements include Cu(II) and Fe(III).

In a particularly preferred embodiment, the compound is the dichloride salt of Fe(III)—Compound 10.

The compound as prepared according to the first or second aspects of the invention may be formulated at various concentrations, depending on the efficacy/toxicity of the compound being used and the purpose for which it is being used. Preferably, the compound is formulated at a concentration of between 0.1 µM and 1 mM, more preferably between 1 µM and 100 µM, between 5 µM and 50 µM, between 10 µM and 50 µM, between 20 µM and 40 µM and most preferably about 30 µM. For in vitro applications, formulations may comprise a lower concentration of a compound, for example between 0.0025 µM and 1 µM.

It will be appreciated by persons skilled in the art that, when used in medicine, the compound will generally be administered in admixture with a suitable pharmaceutical excipient diluent or carrier selected with regard to the intended route of administration and standard pharmaceutical practice (for example, see *Remington: The Science and Practice of Pharmacy*, 19th edition, 1995, Ed. Alfonso Gennaro, Mack Publishing Company, Pennsylvania, USA). Suitable routes of administration are discussed below, and include topical, intravenous, oral, pulmonary, nasal, aural, ocular, bladder and CNS delivery.

For example, for application topically, e.g. to the skin or a wound site, the compounds can be administered in the form of a lotion, solution, cream, gel, ointment or dusting powder (for example, see *Remington*, supra, pages 1586 to 1597). Thus, the compounds can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, e-lauryl sulphate, an alcohol (e.g. ethanol, cetearyl alcohol, 2-octyldodecanol, benzyl alcohol) and water.

In a preferred embodiment, the medicament (e.g. lotion, solution, cream, gel or ointment) is water-based.

Formulations suitable for topical administration in the mouth further include lozenges comprising the active ingredient in a flavoured basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

The medicament for use in the first or second aspects of the invention may also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetra-fluoroethane, a hydrofluoroalkane such as 1,1,1,2-tetrafluoroethane (HFA 134A$^3$ or 1,1,1,2,3,3,3-heptafluoropropane (HFA 227EA$^3$), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" contains at least 1 mg of a compound for delivery to the patient. It will be appreciated that the overall dose with an aerosol will vary from patient to patient and from indication to indication, and may be administered in a single dose or, more usually, in divided doses throughout the day.

Alternatively, other conventional administration routes known in the art may also be employed; for example the medicament for use in the first or second aspects of the invention may be delivered orally, buccally or sublingually in the form of tablets, capsules, ovules, elixirs, solutions or suspensions, which may contain flavouring or colouring agents, for immediate-, delayed- or controlled-release applications. The medicament may also be administered intra-ocularly (see below), intra-aurally or via intracavernosal injection.

The medicament may also be administered parenterally, for example, intravenously, intra-arterially, intraperitoneally, intrathecally, intraventricularly, intrasternally, intracranially, intra-muscularly or subcutaneously (including via an array of fine needles or using needle-free Powderject® technology), or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

The medicament may also be administered by the ocular route, particularly for treating diseases of the eye. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For veterinary use, a compound is administered as a suitably acceptable formulation in accordance with normal veterinary practice and the veterinary surgeon will determine the dosing regimen and route of administration which will be most appropriate for a particular animal.

The medicaments may be stored in any suitable container or vessel known in the art. It will be appreciated by persons skilled in the art that the container or vessel should preferably be airtight and/or sterilised. Advantageously, the container or vessel is made of a plastics material, such as polyethylene.

It will be appreciated that the compounds for use in the first or second aspects of the invention may be employed for killing a number of types of biofilm-forming microorganisms, including bacteria, archaea, protozoa, fungi and algae. Such microorganisms may be resistant to one or more conventional antibiotics, such as methicillin (e.g. MRSA).

In one embodiment, the microorganisms are in a static or slow-growing phase.

It will be further appreciated by skilled persons that the compounds may be used to prevent and/or treat infection with such microorganisms, i.e. the compounds are suitable for prophylactic and/or therapeutic treatment. For example, the compounds may be used to prevent or reduce the spread or transfer of a pathogen to other subjects, e.g. patients, healthcare workers, etc.

In one embodiment of the first and second aspects of the invention, the microorganisms are bacteria.

The bacteria may be Gram positive bacteria, such as those selected from the group consisting of Staphylococci or Streptococci.

For example, the bacteria may be Staphylococci, such as *Staphylococcus aureus* (e.g. methicillin-resistant *Staphylococcus aureus*, MRSA).

Alternatively, the bacteria may be Streptococci, such as *Streptococcus mutans* and/or *Streptococcus sanguis*.

The bacteria may also be Gram negative bacteria, such as *Legionella*.

In an alternative embodiment of the first and second aspects of the invention, the microorganisms are fungi (such as *Candida* spp).

In a further embodiment of the first and second aspects of the invention, the microorganisms are archaea.

In a still further embodiment of the first and second aspects of the invention, the microorganisms are protozoa.

In a still further embodiment of the first and second aspects of the invention, the microorganisms are algae.

Dosages of the compound for use in the first or second aspects of the invention will depend on several factors; including the particular compound used, the formulation, route of administration and the indication for which the compound is used. Typically, however, dosages will range from 0.01 to 20 mg of compound per kilogram of body weight, preferably from 0.1 to 15 mg/kg, for example from 1 to 10 mg/kg of body weight.

It will be appreciated by persons skilled in the art that the compounds described herein may be used to kill, inhibit or prevent the growth of a microbial biofilm in any environment in which such biofilms may be found. Thus, biofilm may be associated with either an inert support or a living support.

In one embodiment, the biofilm is associated with a living support. For example, the biofilm may grow or be susceptible to growth on a surface within the human or animal body.

Thus, the invention provides a compound as defined above for use in the treatment or prevention of a condition associated with the presence or growth of a biofilm.

For example, the compounds described herein may be used to treat or prevent a disorder or condition associated with the growth of a microbial biofilm at one of the following sited within the body:
(a) The oral cavity, including the surfaces of the teeth and gums (for example, dental plaque, gingivitis, endodontic infections, oral candidiasis, oral aspergillosis, periodontitis).
   However, in one embodiment, the compounds are not used for the curative and/or prophylactic treatment of periodontitis or other dental infections.
(b) The urinary tract (for example, cystitis).
(c) The sinuses (for example, chronic sinusitis).
(d) The ear (for example, middle ear infections).
   However, in one embodiment, the compounds are not used for the curative and/or prophylactic treatment of otitis.
(e) The heart (for example, endocarditis).
(f) The prostate (for example, chronic bacterial prostatitis).
(g) The bone (for example, osteomyelitis)
   However, in one embodiment, the compounds are not used for the curative and/or prophylactic treatment of osteomyelitis.
(h) The lungs (for example, infections in cystic fibrosis such as pneumonia)
   However, in one embodiment, the compounds are not used for the curative and/or prophylactic treatment of *Pseudomonas* infection in cystic fibrosis patients.
(i) The kidneys (for example, infectious kidney stones and in peritoneal dialysis).
(j) The skin.
   However, in one embodiment, the compounds are not used for the curative and/or prophylactic treatment of atopic dermatitis.

In a further embodiment, the biofilm is associated with an inert support. Thus, the biofilm may grow or be susceptible to growth on the surface of a device implanted or otherwise inserted within the human or animal body.

For example, the compounds described herein may be used to treat or prevent an infection associated with the growth of a microbial biofilm on one of the following inert surfaces within the body:
(a) A catheter (for example, for intravascular or urinary tract use).
(b) A stent (for example, a coronary stent).
(c) A shunt (for example, a cerebrospinal shunt).
(d) An intubating or tracheotomy tube.
(e) An opthalmic device (for example, contact lenses, scleral buckles and intraocular lenses).
(f) A joint prosthesis (i.e. arthroplasty and implantation of other orthopaedic devices).
(g) An artificial heart valve.
(h) A breast implant.

Thus, it will be appreciated that the compounds as described herein are particularly suited to the treatment and prevention of nosocomial infections.

In a preferred embodiment, the compounds for use in the first or second aspects of the invention are used in combination with conventional antimicrobial agents. For example, the compounds may be used in combination with one or more of the following conventional antibiotics: anti-bacterial agents, for example natural and synthetic penicillins and cephalosporins, sulphonamides, erythromycin, kanomycin, tetracycline, chloramphenicol, rifampicin and including gentamicin, ampicillin, benzypenicillin, benethamine penicillin, benzathine penicillin, phenethicillin, phenoxy-methyl penicillin, procaine penicillin, cloxacillin, flucloxacillin, methicillin sodium, amoxicillin, bacampicillin hydrochloride, ciclacillin, mezlocillin, pivampicillin, talampicillin hydrochloride, carfecillin sodium, piperacillin, ticarcillin, mecillinam, pirmecillinan, cefaclor, cefadroxil, cefotaxime, cefoxitin, cefsulodin sodium, ceftazidime, ceftizoxime, cefuroxime, cephalexin, cephalothin, cephamandole, cephazolin, cephradine, latamoxef disodium, aztreonam, chlortetracycline hydrochloride, clomocycline sodium, demeclocydine hydrochloride, doxycycline, lymecycline, minocycline, oxytetracycline, amikacin, framycetin sulphate, neomycin sulphate, netilmicin, tobramycin, colistin, sodium fusidate, polymyxin B sulphate, spectinomycin, vancomycin, calcium sulphaloxate, sulfametopyrazine, sulphadiazine, sulphadimidine, sulphaguanidine, sulphaurea, capreomycin, metronidazole, tinidazole, cinoxacin, ciprofloxacin, nitrofurantoin, hexamine, streptomycin, carbenicillin, colistimethate, polymyxin B, furazolidone, nalidixic acid, trimethoprim-sulfamethox-azole, clindamycin, lincomycin, cycloserine, isoniazid, ethambutol, ethionamide, pyrazinamide and the like; anti-fungal agents, for example miconazole, ketoconazole, itraconazole, fluconazole, amphotericin, flucytosine, griseofulvin, natamycin, nystatin, and the like; and anti-viral agents such as acyclovir, AZT, ddI, amantadine hydrochloride, inosine pranobex, vidarabine, and the like.

In a further preferred embodiment, the medicaments comprise and/or are co-administered with penetration enhancing agents, such as poly-(ethyleneimine), or antibiotic agents which exhibit such penetration-enhancing capability (e.g. polymyxin or colistin).

The compounds for use in the first and second aspects of the invention may also be employed to kill, inhibit or prevent the growth of microbial biofilms in vitro. For example, the compounds may also be used in the form of a sterilising solution or wash to prevent the growth of microbial biofilms on a surface or substrate, such as in a domestic environment (e.g. kitchen work surfaces, showers, pipes, floors, etc.) or a commercial or industrial environment (e.g. within cooling systems, pipes, floor surfaces, etc.) environment.

Preferably, such a medicament comprises the antimicrobial compound in solution at a concentration of 1 to 100 µg/ml.

Preferably, the solution further comprises a surface-active agent or surfactant. Suitable surfactants include anionic surfactants (e.g. an aliphatic sulphonate), amphoteric and/or zwitterionic surfactants (e.g. derivatives of aliphatic quaternary ammonium, phosphonium and sulfonium compounds) and nonionic surfactants (e.g. aliphatic alcohols, acids, amides or alkyl phenols with alkylene oxides)

Conveniently, the surface-active agent is present at a concentration of 0.5 to 5 weight percent.

In both in vitro and in vivo uses, the compounds for use in the first and second aspects of the invention are preferably exposed to the target surface for at least five minutes. For example, the exposure time may be at least 10 minutes, 20 minutes, 30 minutes, 40 minutes, 50 minutes, 1 hour, 2 hours, 3, hours, 5 hours, 12 hours and 24 hours.

A third aspect of the invention provides a use of a compound as described herein for killing, inhibiting or preventing the growth of bacteria in a slow-growing phase.

A fourth aspect of the invention provides a use of a compound as described herein for killing, inhibiting or preventing the growth of bacteria in a static phase.

Thus, the invention provides a compound as defined above for use in the treatment or prevention of a condition associated with the presence or growth of bacteria in a slow-growing phase or static phase.

As demonstrated in the accompanying Examples, the compounds of the invention can be used to kill, inhibit or prevent the growth of bacteria in a slow-growing phase or static phase.

It will be understood by those skilled in the art that, under certain conditions (such as environmental and/or physiological conditions), bacteria may enter a slow-growing phase (in which the growth rate of the bacteria is reduced) and/or a static phase (in which growth of the bacteria cannot be detected). By "growth", we include the replication and/or reproduction and/or division of a bacterial cell (or population of such cells), and also include the reproduction and/or replication of cellular components and/or chemicals within a bacterial cell (or population of such cells).

It is well known that the growth rate will vary between bacteria, such that different genera, species, types and strains of bacteria may have different growth rates. Growth rate is also determined by the particular environmental conditions to which the bacteria of interest are subjected, and will vary depending on the content and composition of nutrients in the surrounding medium, and other factors such as temperature, aeration, agitation, light and pH.

The optimum rate of growth for bacteria may be determined in vitro (e.g. in a laboratory test tube or flask culture) by measuring the growth rate during the exponential growth phase under standard conditions (i.e. a defined culture medium and temperature, aeration, agitation, light and pH).

Depending on the bacteria, the time required for a bacterial cell to divide and the population to double in size ("generation time") varies from about 12 minutes to 24 hours or more. Methods for calculating the generation time of bacteria are well known in the art (see, for example, Brock et al., Biology of Microorganisms, 6$^{th}$ Ed, 1991, Prentice Hall, and http://www.textbookofbacteriology.net/growth.html).

The generation time for *E. coli* in the laboratory is 15-20 minutes, but in the intestinal tract is estimated to be 12-24 hours. For most known bacteria that can be cultured, generation times range from about 15 minutes to 1 hour (although symbionts such as *Rhizobium* and lithotrophs, such as the nitrifying bacteria, tend to have longer generation times).

Some bacteria that are pathogens, such as *Mycobacterium tuberculosis* and *Treponema pallidum*, have especially long generation times. Generation times for a few bacteria are shown overleaf:

| Bacterium | Medium | Generation Time (mins) |
|---|---|---|
| *Escherichia coli* | Glucose-salts | 17 |
| *Bacillus megaterium* | Sucrose-salts | 25 |
| *Streptococcus lactis* | Milk | 26 |
| *Streptococcus lactis* | Lactose broth | 48 |
| *Staphylococcus aureus* | Heart infusion broth | 27-30 |
| *Lactobacillus acidophilus* | Milk | 66-87 |
| *Rhizobium japonicum* | Mannitol-salts-yeast extract | 344-461 |
| *Mycobacterium tuberculosis* | Synthetic | 792-932 |
| *Treponema pallidum* | Rabbit testes | 1980 |

It will be understood that bacteria in a slow-growing phase or a static phase can be identified by comparison to the optimum growth rate of that bacteria in vitro (e.g. in a laboratory test tube or flask culture under standard conditions of culture medium, temperature, aeration, agitation, light and pH).

For example, a slow growth rate may be less than 50% of the optimum growth rate of that bacteria, such as less than 60% or 70% or 80% or 90% or 95% of the optimum growth rate of that bacteria in vitro).

In a preferred embodiment, the bacteria according to the third or fourth aspect of the invention are as described above (in relation to the first aspect of the invention). Preferably, the bacteria according to the third or further aspect of the invention are on or in the body of a living mammal, such as a human, for example, as described above (in relation to the first aspect of the invention).

It is known that infections (such as infections in mammals) can be caused by bacteria in a slow-growing or static phase selected from the group consisting or comprising:

mycobacteria (In: Laboratory diagnosis of bacterial infections; edited by Nevoi Cimolai and published by Informa Healthcare, 2001, p 384-5);

actinomycetes (In: Laboratory diagnosis of bacterial infections; edited by Nevoi Cimolai and published by Informa Healthcare, 2001, p 384-5);

*Staphylococcus aureus* small colony variants (Vaudaux P et al. Difficult to diagnose and difficult to treat, Clinical Infectious Diseases (2006); 43: 968-70); and brucellae. (Guerra H. The brucellae and their success as pathogens. Crit. Rev. Microbiol. (2007); 33(4): 325-31).

Accordingly, in a preferred embodiment, the third and fourth aspects of the invention comprise a use in which the bacteria in a slow-growing phase or a static phase are selected from the list consisting or comprising: mycobacteria; actinomycetes; *Staphylococcus aureus* small colony variants; brucellae.

A fifth aspect of the invention provides a method for treating a patient suffering from or susceptible to a disease or condition associated with or caused by a microbial biofilm, the method comprising administering to the patient a compound as described herein.

A sixth aspect of the invention provides a method for treating a patient suffering from or susceptible to a disease or condition associated with or caused by a bacteria in a slow-growing phase, the method comprising administering to the patient a compound as described herein.

As discussed above, it is known that infections (such as infections in mammals) can be caused by bacteria in a slow-growing or static phase selected from the group consisting or comprising: mycobacteria; actinomycetes; *Staphylococcus aureus* small colony variants; and brucellae.

Accordingly, in a preferred embodiment, the fifth aspect of the invention comprises a method in which the bacteria in a slow-growing phase or a static phase are selected from the list consisting or comprising: mycobacteria; actinomycetes; *Staphylococcus aureus* small colony variants; brucellae.

A seventh aspect of the invention provides a method for treating a patient suffering from or susceptible to a disease or condition associated with or caused by a bacteria in a static phase, the method comprising administering to the patient a compound as described herein.

It will be appreciated by persons skilled in the art that the compounds may be used in the form of photodynamic therapy or, alternatively, their inherent antimicrobial activity may be exploited (as described in International Patent Application Nos: PCT/GB2003/005649 [WO 2004/056828] and PCT/GB2005/002457 [WO 2006/000765], the disclosures of which are incorporated herein by reference.

The compounds may be formulated and administered using methods well known in the art. For example, the compound may be administered orally, parenterally or topically.

As discussed above, the biofilm may be on a living support in the oral cavity, urinary tract, sinuses, ear, heart, prostate, bone, lungs, kidneys and/or skin.

Alternatively, the biofilm may be on an inert support within body, such as a catheter, a stent, a shunt, an intubating or tracheotomy tube, an opthalmic device, a joint prosthesis, an artificial heart valve and/or a breast implant.

An eighth aspect of the invention provides an implantable medical device which is impregnated, coated or otherwise treated with a compound as described herein.

For example, the implantable medical device may be selected from the group consisting of intravascular devices, catheters, shunts, intubating and tracheotomy tubes, opthalmic devices, joint prostheses, artificial heart valves and breast implants. By "implantable device" we include devices attached to surface of body, e.g. contact lenses.

Preferably, the implantable medical device is packaged in a sealed and sterile container prior to use.

The invention further provides a method of making an implantable medical device according to the eighth aspect of the invention, the method comprising treating an untreated implantable medical device, or the components or ingredients thereof, with a compound as described herein.

By 'treating' in the context of this aspect of the invention we mean that the compound is coated, impregnated, covalently bound to or otherwise admixed with an untreated implantable medical device, or the components or ingredients thereof.

Preferably, the implantable medical device is coated with the compound. By 'coated' we mean that the compound is applied to the surface of the implantable medical device. Thus, the implantable medical device may be painted or sprayed with a solution comprising a compound. Alternatively, the implantable medical device may be dipped in a reservoir of the compound in solution.

For example, the implantable medical device may be incubated overnight at 4° C. in a solution comprising a compound as described herein. Alternatively, the compound may be immobilised on the implantable medical device by evaporation or by incubation at room temperature.

Alternatively, the implantable medical device is impregnated with the compound. By 'impregnated' we mean that the compound is incorporated or otherwise admixed with the components or ingredients of the implantable medical device during manufacture, such that it is distributed throughout the assembled device.

Preferred, non-limiting embodiments of the invention will now be described by way of example, with reference to the accompanying drawings in which.

NHDF were incubated with different concentrations of Compound 10 for 5 min, 1 h and 4 h (0 µM, 0.01 µM, 0.1 µM, 1.0 µM, 10 µM). Cells were then incubated for 24 h in the dark. Toxicity was tested by standard MTT-assay. Cell viability was normalised to one, which means, the values of control cells were normalised to one. Grey dotted line: 5 min incubation; black dotted: 1 h incubation; black line: 4 h incubation; (n=3, mean±SD).

Figure 3:
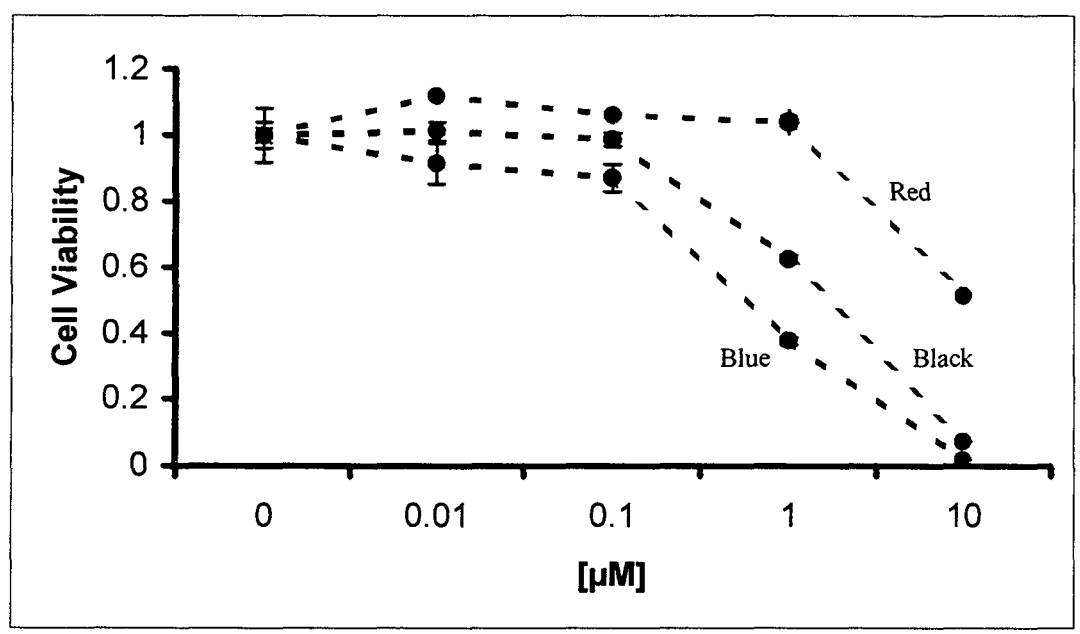

FIG. 3 shows cell toxicity of normal human epidermal keratinocytes after 5 minutes, 1 hour and 4 hours incubation with Compound 10.

NHEK were incubated with different concentrations of Compound 10 for 5 min, 1 h and 4 h (0 µM, 0.01 µM, 0.1 µM, 1.0 µM, 10 µM). Cells were then incubated for 24 h in the dark. Toxicity was tested by standard MTT-assay. Cell viability was normalised to one, which means, the values of control cells were normalised to one. Red dotted line: 5 min incubation; black dotted: 1 h incubation; blue dotted: 4 h incubation only; (n=3, mean±SD).

Figure 4A:
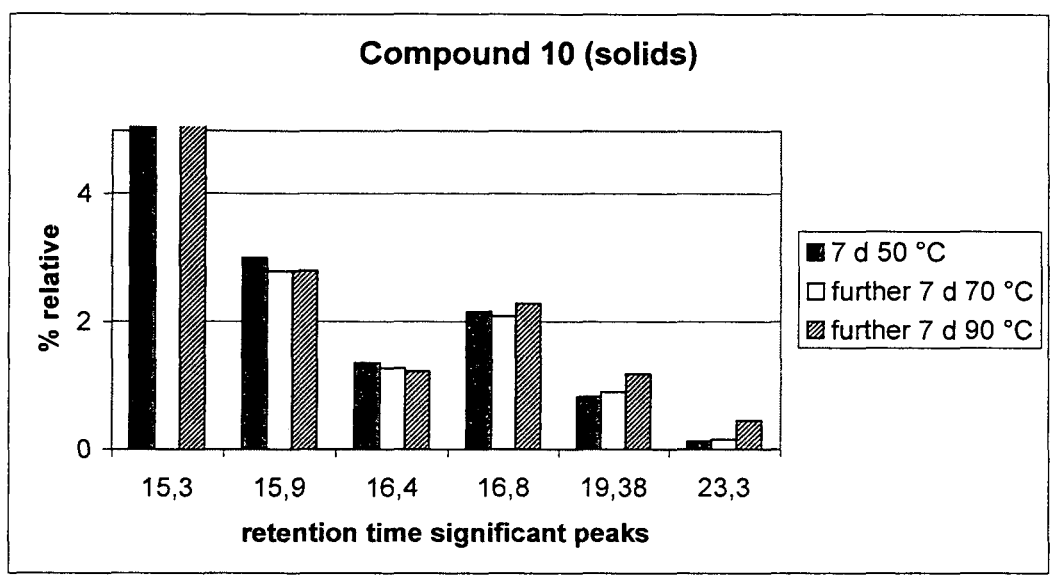
Figure 4B:
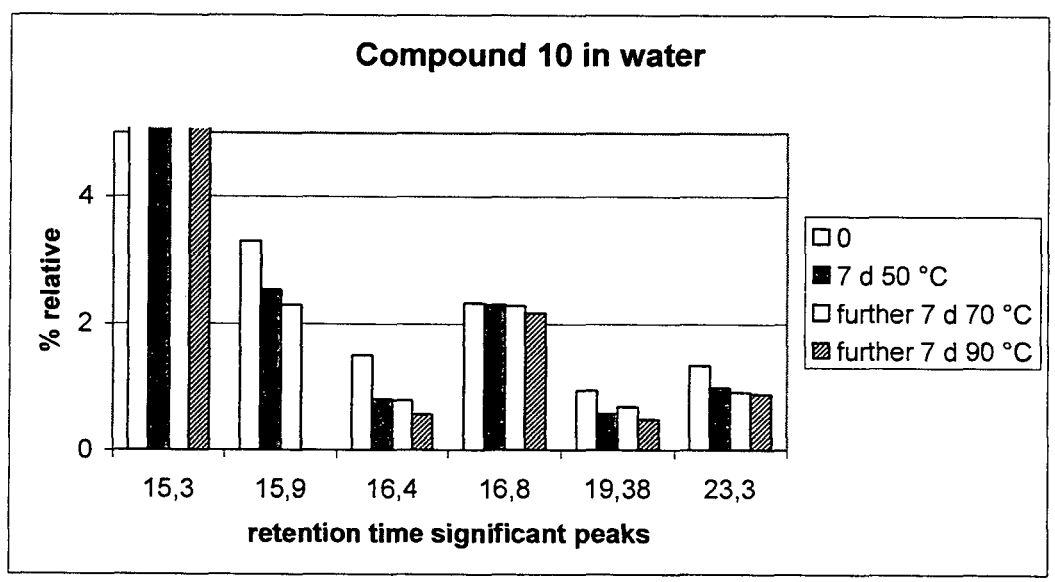
Figure 4C:
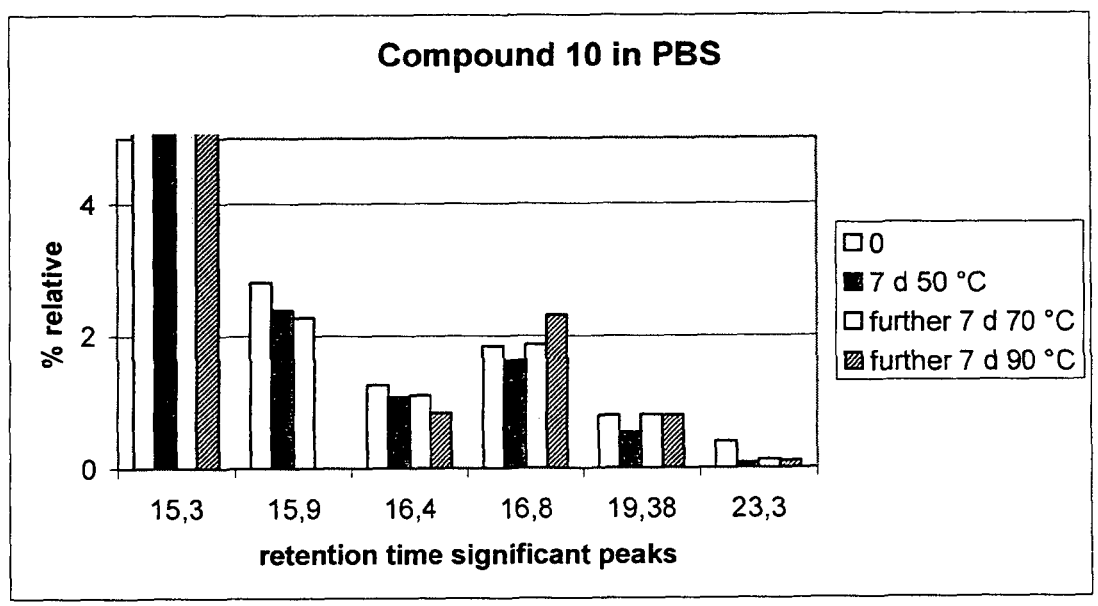

FIG. 4 shows the chemical stability of Compound 10 formulated (A) as a solid, (B) in water and (C) in PBS.

Figure 5:
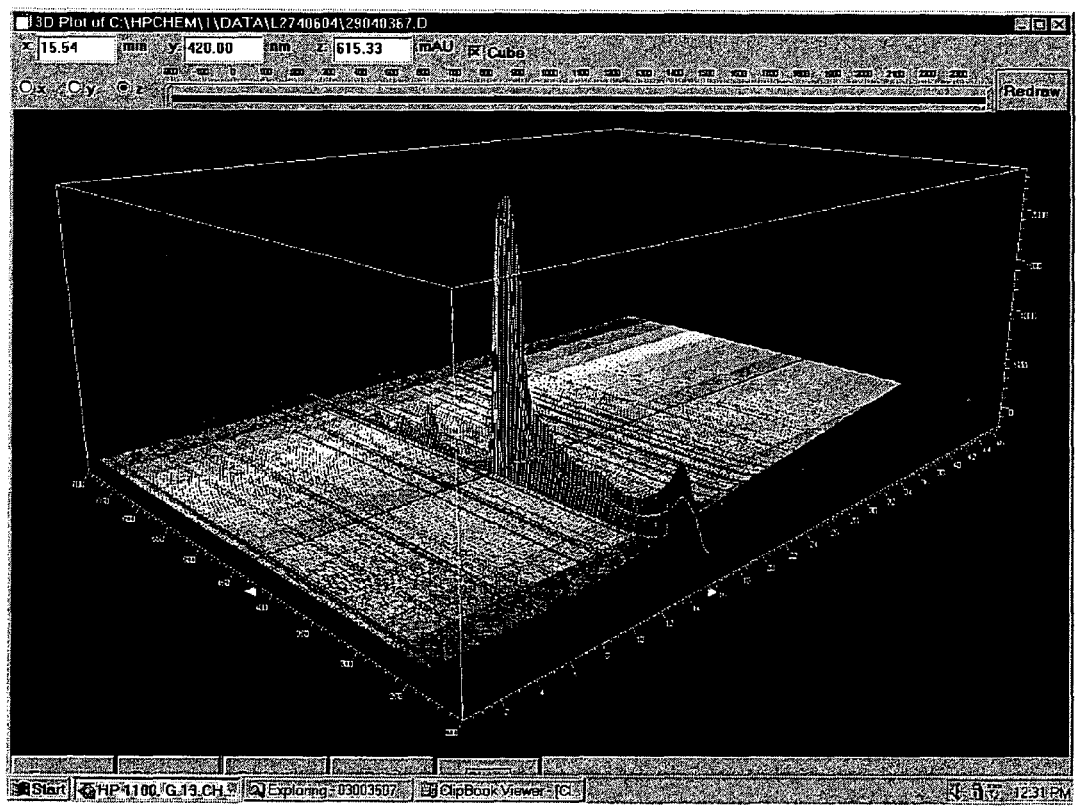
Figure 6A:
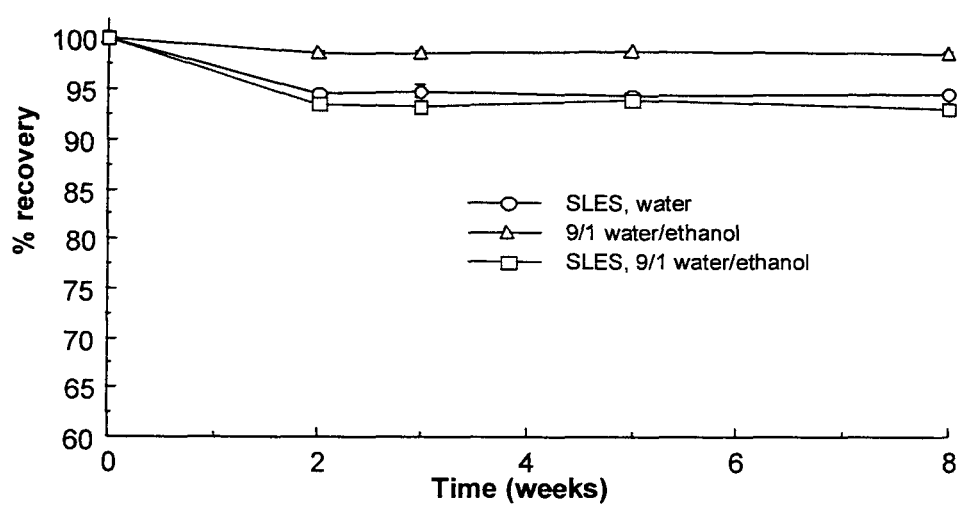
Figure 6B:
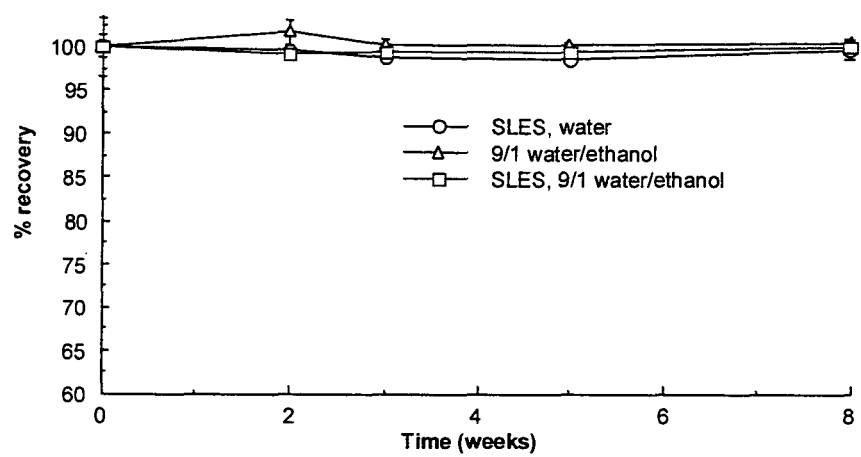
Figure 6C:
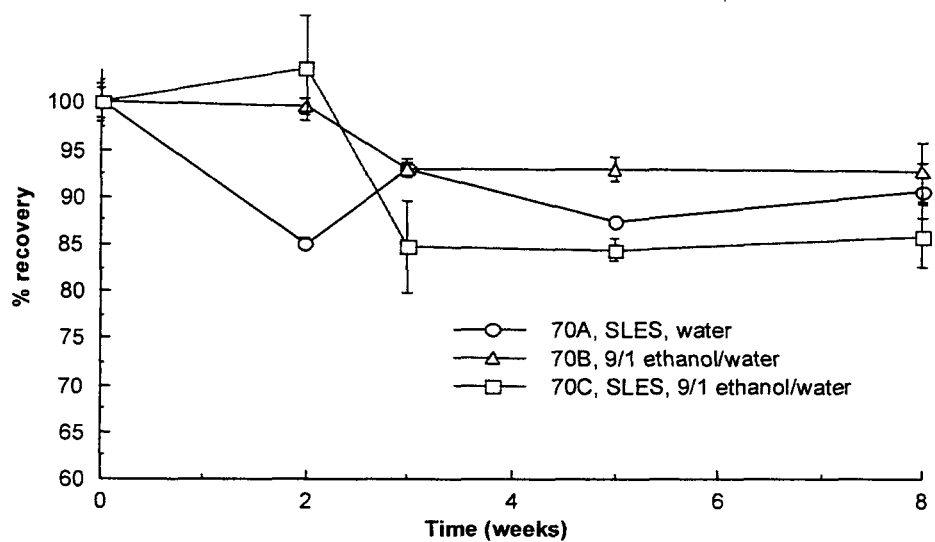
Figure 6D:
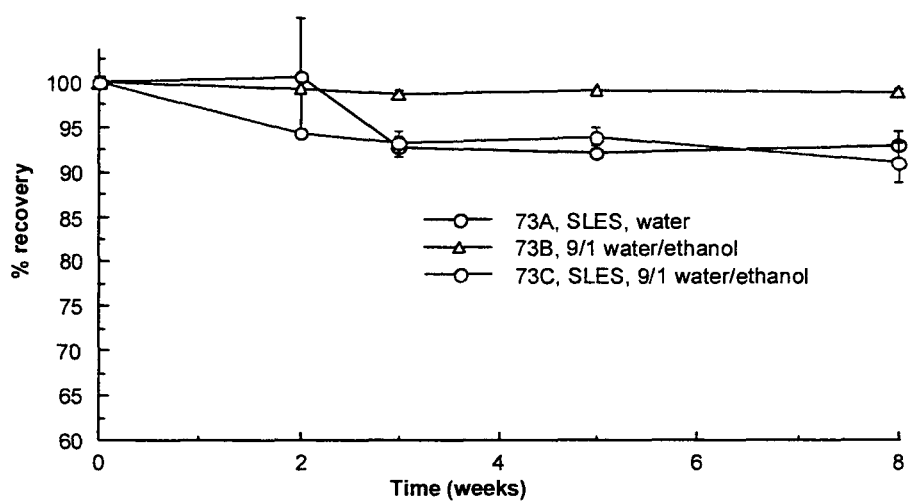

FIG. 5 shows a 3D plot of the stability (measured by HPLC) of Compound 10 after 21 days in PBS buffer.

FIG. 6 shows the stability over 8 weeks of various formulations of (A) Compound 1, (B) Compound 8, (C) Compound 12 and (D) Compound 10.

Figure 7A:
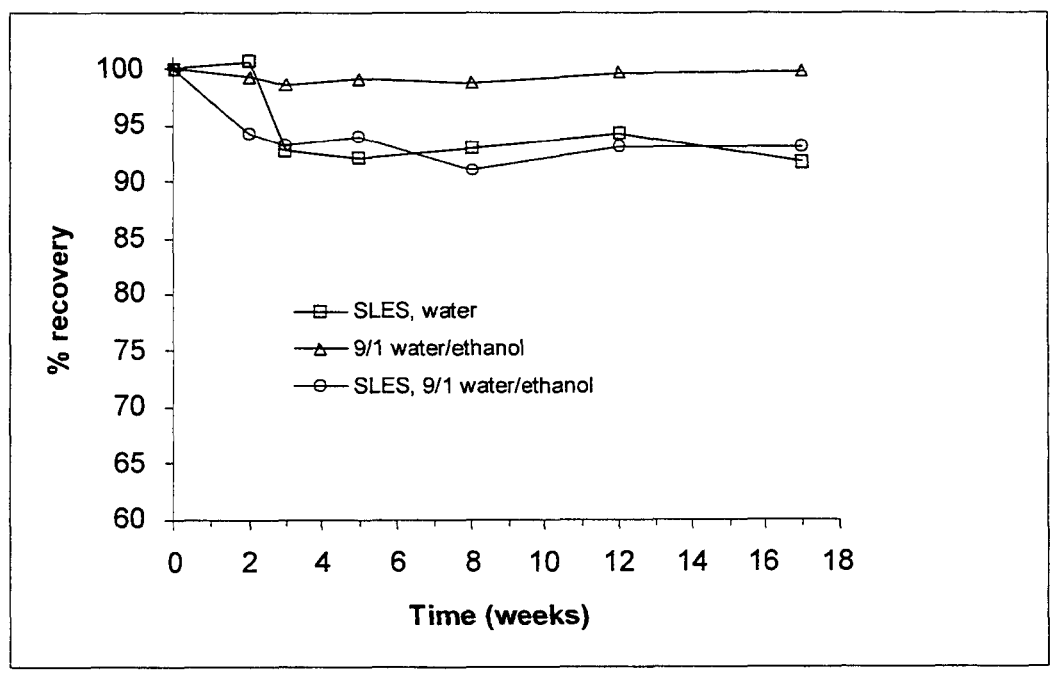
Figure 7B:
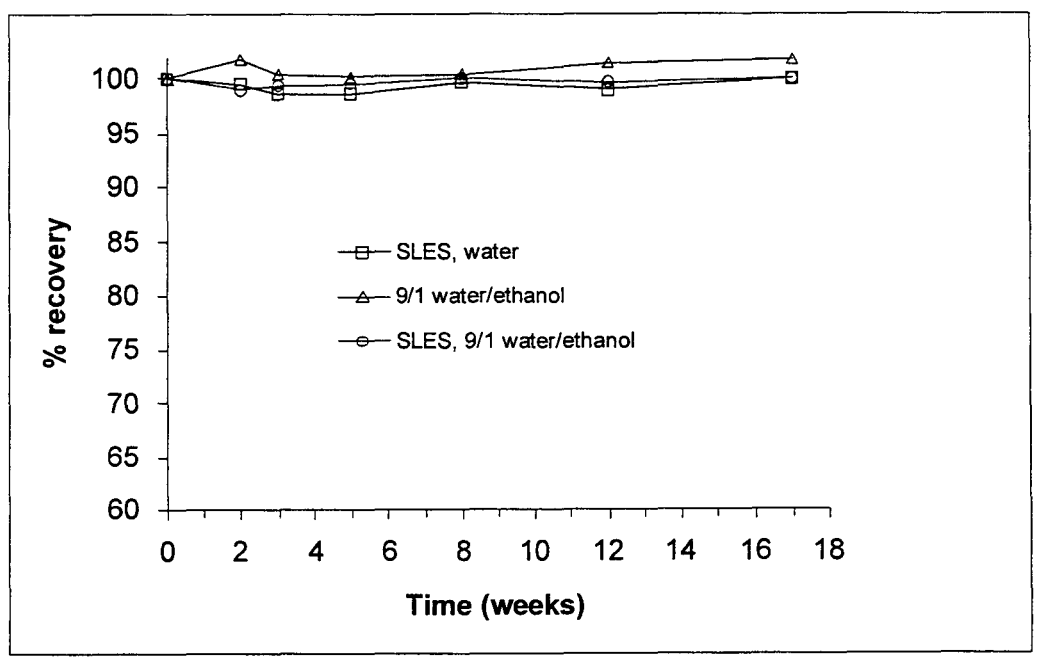

FIG. 7 shows the extended stability over 17 weeks of various formulations of (A) Compound 10 and (B) Compound 8.

Figure 8:
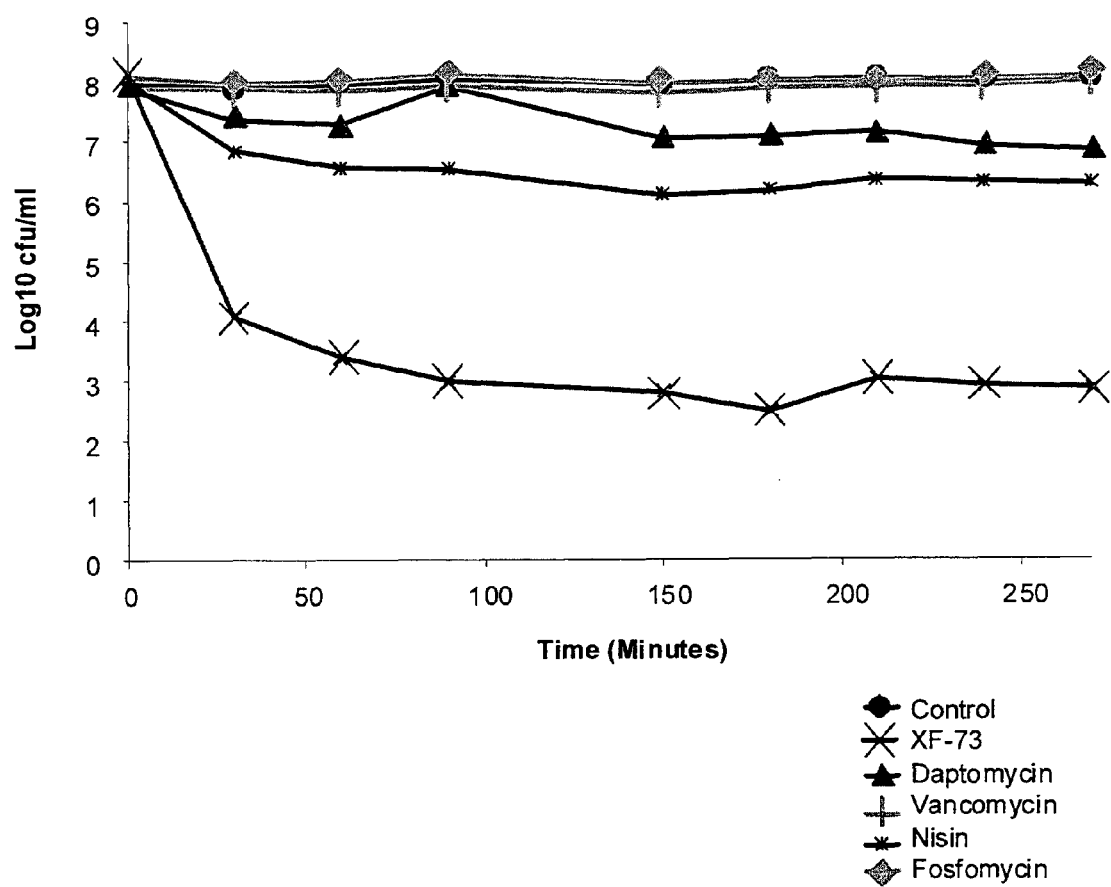

FIG. 8 shows the effects of Compound 10 ("XF-73") and control agents at 4×MIC against *S. aureus* SH1000 cold-cultures.

Figure 9:
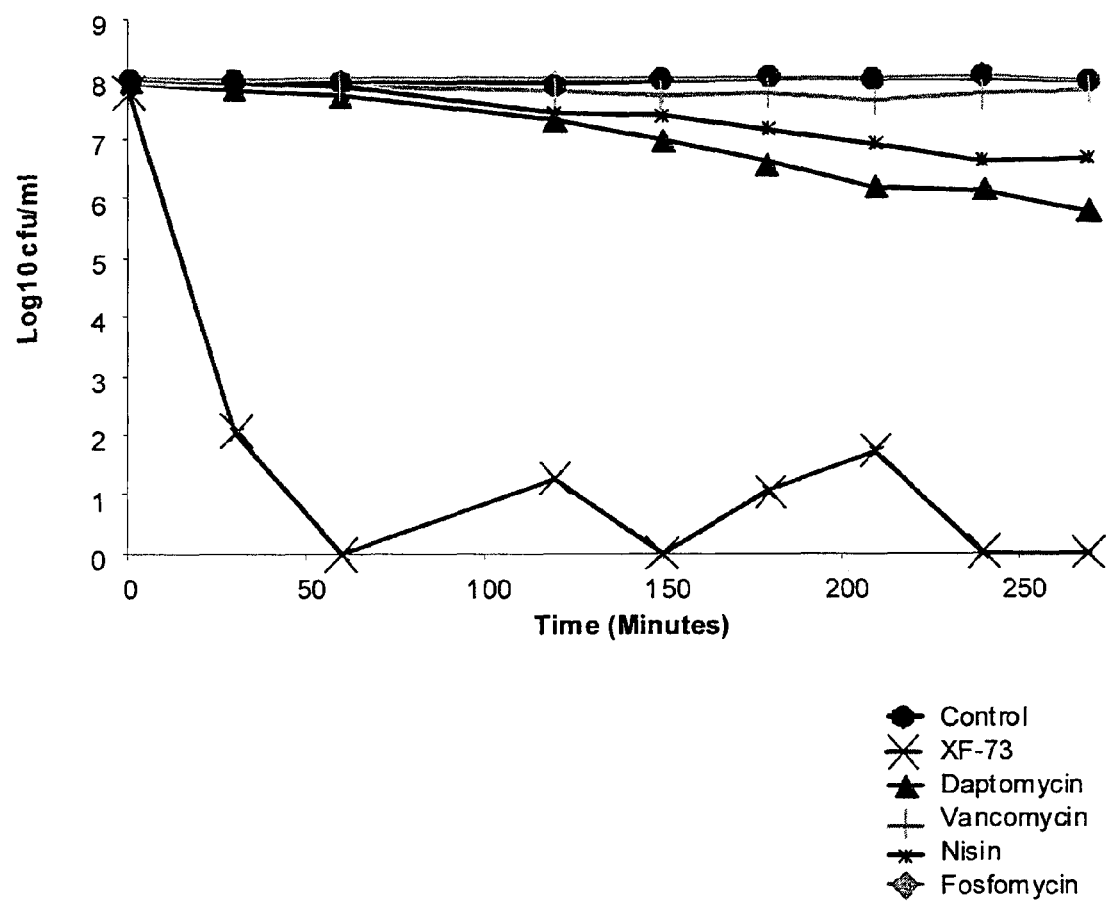

FIG. 9 shows the effects of Compound 10 ("XF-73") and control agents at 4×MIC against stringent† *S. aureus* SH1000 cultures.

Figure 10:
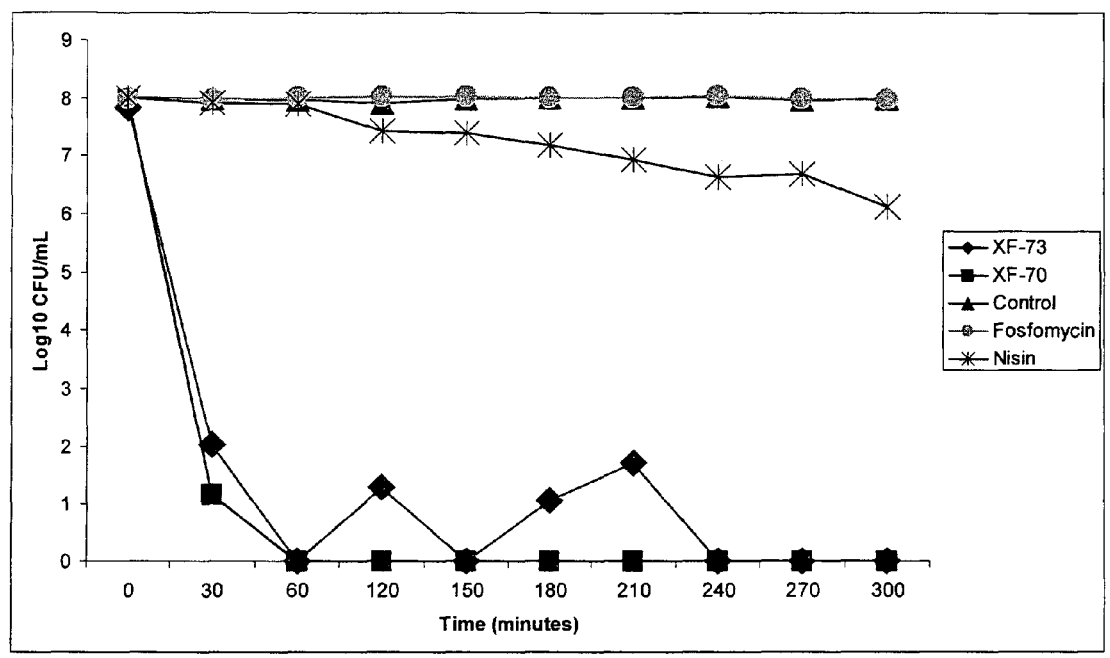

FIG. 10 shows the effects of Compound 12 ("XF-70") and Compound 10 ("XF-73") and comparator agents (at 4×MIC) on the viability of stringent *S. aureus* SH1000 cultures. Mupirocin (5 ug/ml) was added at time −30 minutes to induce the stringent response, followed by other inhibitors and drugs at time zero.

Figure 11:
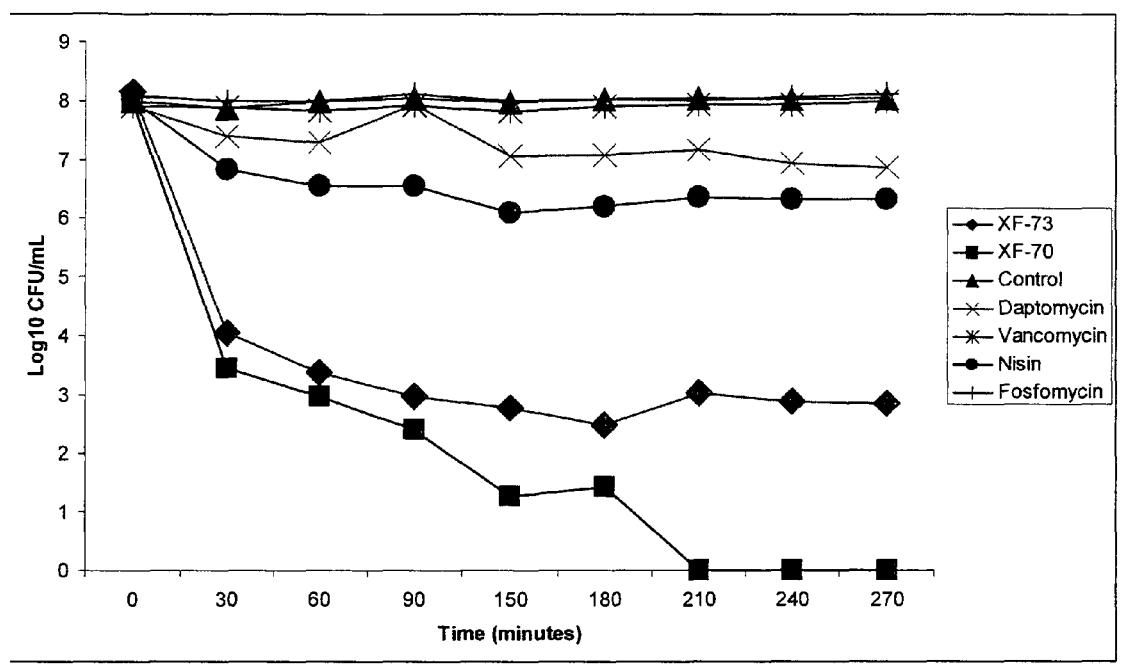

FIG. 11 shows the effects of Compound 12 ("XF-70") and Compound 10 ("XF-73") and comparator agents (at 4×MIC) on the viability of *S. aureus* SH1000 held at 4° C. in Mueller-Hinton Broth.

Figure 12:
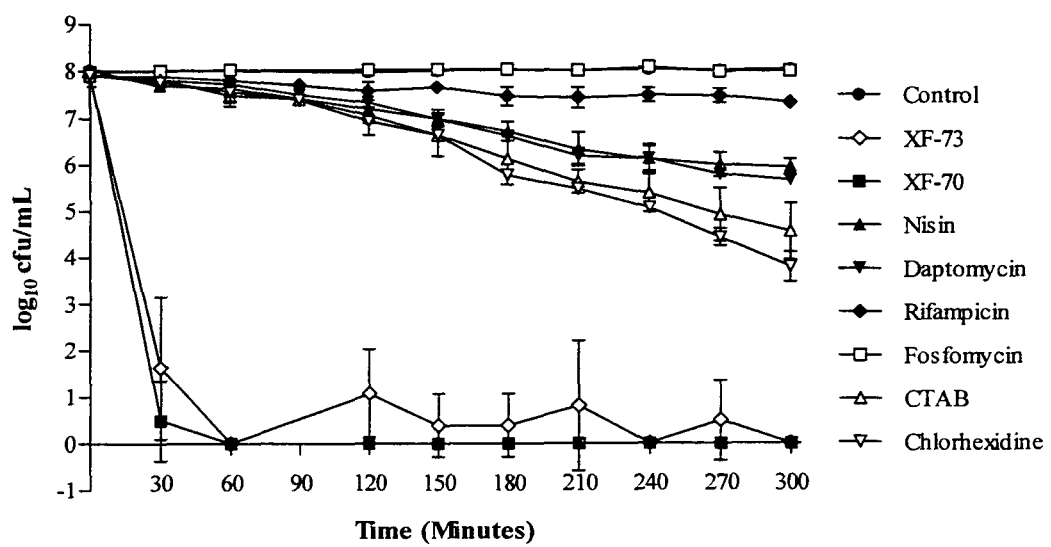

FIG. 12 shows the killing kinetics of Compound 10 ("XF-73"), Compound 12 ("XF-70") and a number of antimicrobial agents against *S. aureus* SH1000 cells expressing the stringent response. Values shown are the means and standard deviations of three replicates from three independent experiments.

Figure 13:
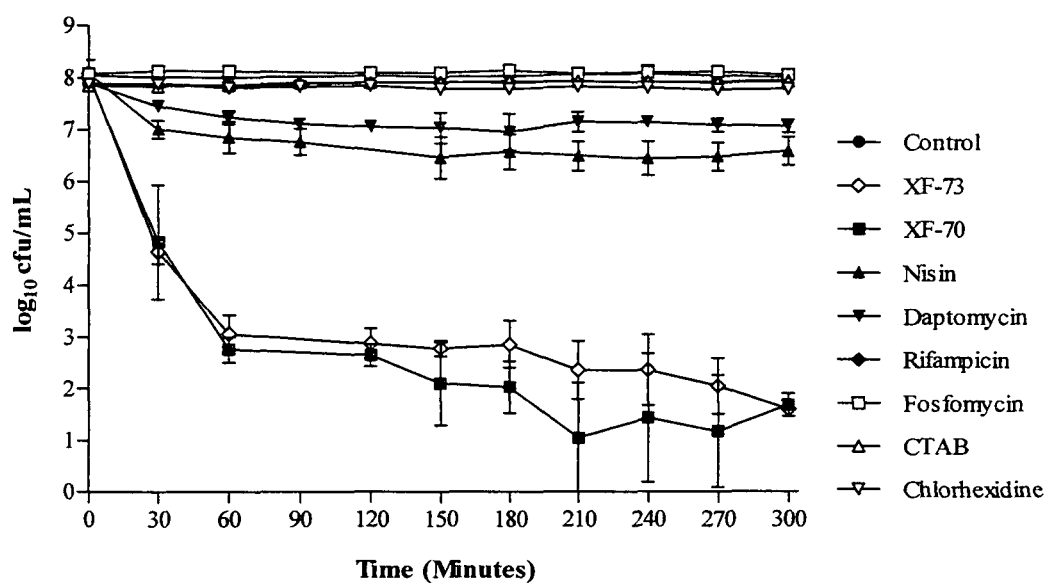

FIG. 13 shows the killing kinetics of Compound 10 ("XF-73"), Compound 12 ("XF-70") and a number of antimicrobial agents against *S. aureus* SH1000 cells in cold cultures. Values shown are the means and standard deviations of three replicates from three independent experiments.

Figure 14:
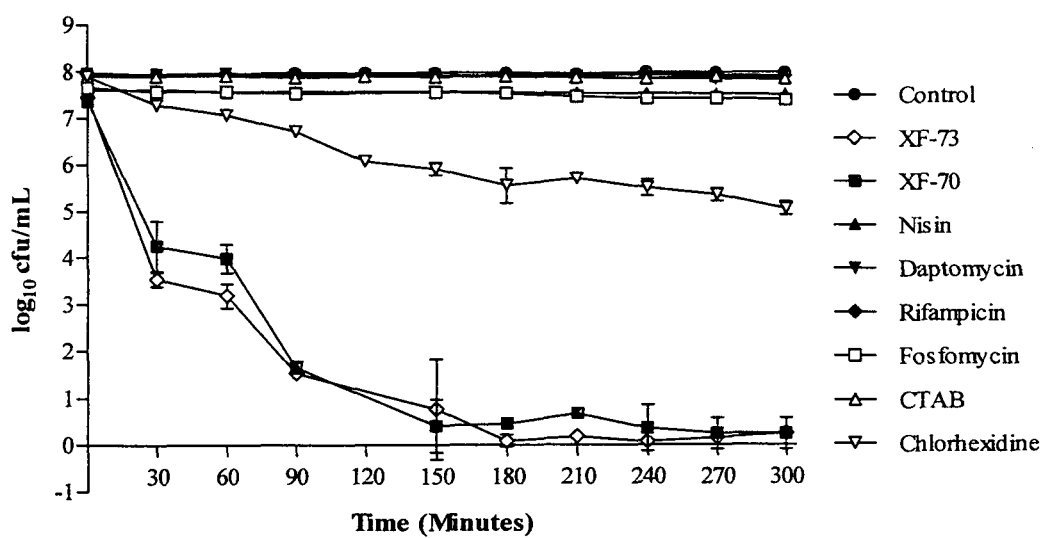

FIG. 14 shows the killing kinetics of Compound 10 ("XF-73"), Compound 12 ("XF-70") and a number of antimicrobial agents against S. aureus SH1000 cells in the early stationary phase. Values shown are the means and standard deviations of three replicates from three independent experiments.

Figure 15:
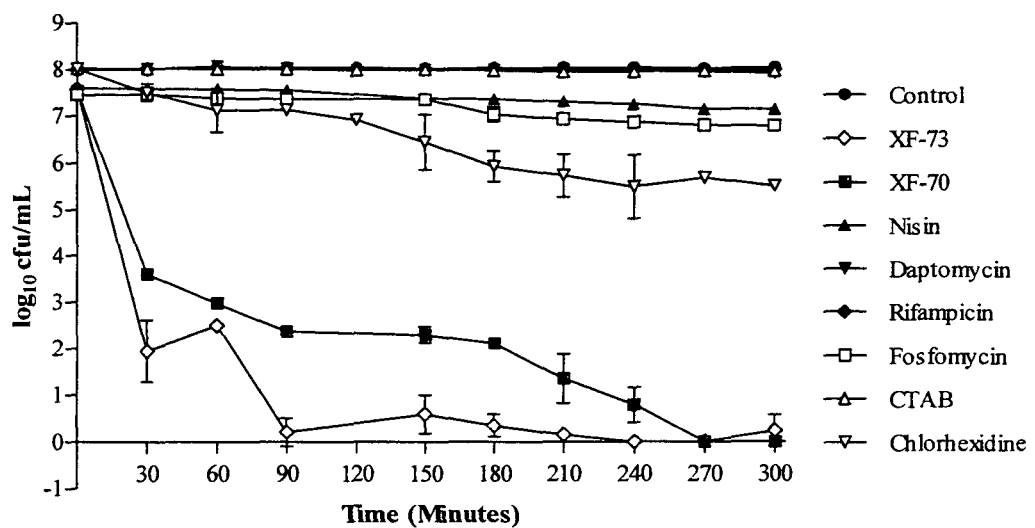

FIG. 15 shows the killing kinetics of Compound 10 ("XF-73"), Compound 12 ("XF-70") and a number of antimicrobial agents against S. aureus SH1000 cells in the mid stationary phase. Values shown are the means and standard deviations of three replicates from three independent experiments.

Figure 16:
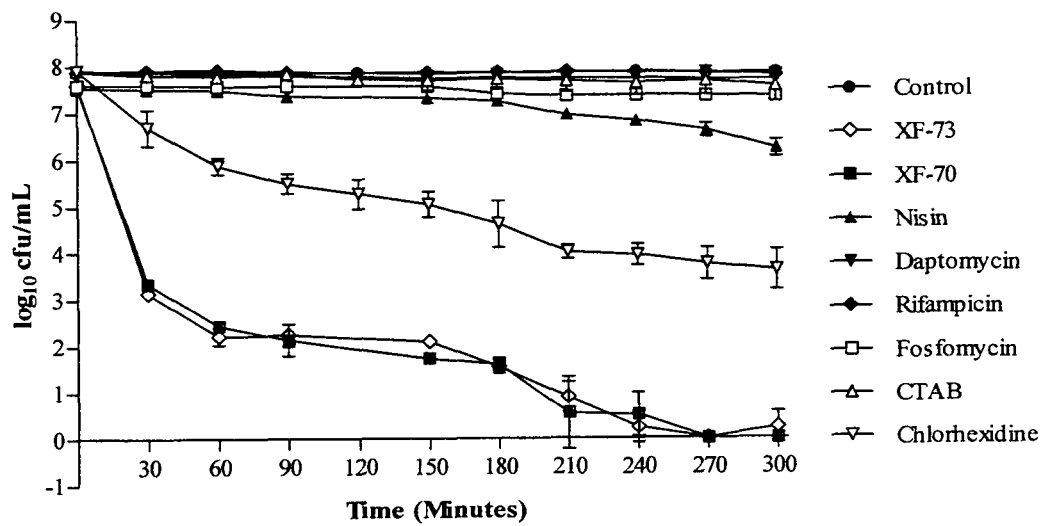

FIG. 16 shows the killing kinetics of Compound 10 ("XF-73"), Compound 12 ("XF-70") and a number of antimicrobial agents against S. aureus SH1000 cells in the late stationary phase. Values shown are the means and standard deviations of three replicates from three independent experiments.

EXAMPLES

Example A

Synthesis of Exemplary Compounds

Materials and Methods
NMR-Measurements

Proton NMR spectra were recorded on a Bruker B-ACS60 (300 MHz) instrument using TMS as internal standard. The chemical shifts are given in ppm and coupling constants in Hz in the indicated solvent. Some abbreviation for NMR: singlet (s), broad singlet (bs), doublet (d), triplet (t), quartet (q), quintet (quint), multiplet (m).

Chemicals

All solvents and reagents were purchased from Aldrich, Fluka, Merck and Lancaster and used without further purification.

Dipyrrolmethane was prepared as described by C. Brücker et al., J. Porphyrins Phthalocyanines, 2 455 (1998).

Chromatography

Column chromatography was carried out using silica gel (Merck Silicagel 60, Fluka 60, 0.040-0.063 mm) and Sephadex LH-20 (Pharmacia). All solvents (Synopharm) for chromatography were technical pure grade.

Abbreviations

DDQ: 2,3-dichloro-5,6-dicyano-p-benzoquinone
DMF: N,N-dimethylformamide
TFA: trifluoroacetic acid Synthesis Routes for Test Compounds The following test compounds were synthesised as described in WO 2004/056828, WO 2006/000765 and WO 2007/074340 (the disclosures of which are incorporated herein by reference):

Exemplary Compounds for Use in the Invention

Compounds 6, 8 to 10, 12, 23, 25, 28, 31 and 32.

Reference Compounds (for Use as Comparative Controls)

Compounds 1, 3, 16, 19, 26, 29, 33, 36, 37, 39, 41 and 46 to 51.

Chemical Intermediates

Compounds 2, 4, 5, 7, 11, 13 to 15, 17, 18, 20 to 22, 24, 27, 30, 34, 35, 38, 40 and 42 to 45.

Compound 6

5-[3,5-bis-(3-Trimethylammonio-propyloxy)-phenyl]-15-undecyl-porphyrin dichloride

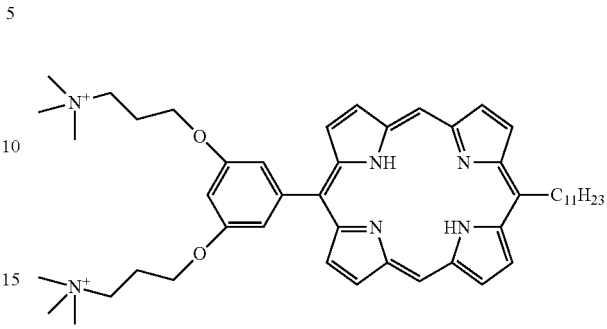

To a vigorously-stirred suspension of Compound 5 (80 mg, 0.14 mmol) and $K_2CO_3$ (230 mg, 1.7 mmol) in DMF (30 mL) is added (1-bromopropyl)-trimethylammonium bromide (0.3 g, 16.6 mmol) at 50° C. The mixture is stirred at this temperature for 18 h. After removal of the DMF under reduced pressure, the residue obtained is dissolved in methanol (5 mL) and filtered through a pad of silica gel (depth 2 cm) supported on a steel frit (diameter 3.5 cm). After washing the pad with methanol (ca. 1 L) the crude product is eluted with acetic acid:methanol:water (3:2:1, by vol.). Appropriate fractions are collected and, after evaporation of the solvent under reduced pressure, the residue obtained is purified by chromatography on a column (2.5×40 cm) of Sephadex LH-20 eluting with n-butanol:water:acetic acid (5:4:1, by vol., upper phase). After removal of the solvent from appropriate fractions under reduced pressure, the residue obtained is dissolved in methanol (5 mL) and the solution is passed through a short column (3.5×20 cm) of anion exchange resin (Amberlite IRA 400, chloride form). After collection of the eluate, solvent is removed under reduced pressure and the residue obtained is dried under high vacuum to yield the dichloride salt as a violet solid.

$^1$H-NMR:

$\delta_H$ (300 Mz, $CD_3OD$): 0.75 (t, $^3J$ 7.5 Hz, 3 H), 1.05-1.20 (m, 14 H), 1.45-1.50 (m, 2 H), 2.05-2.15 (m, 4 H), 2.15-2.20 (m, 2 H), 2.95 (s, 18 H), 3.35-3.45 (m, 4 H), 3.95 (t, $^3J$ 7.5 Hz, 4 H), 4.55 (t, $^3J$ 7.5 Hz, 2 H), 6.85 (m, 1 H), 7.35 (m, 2 H), 8.85-8.90, 9.15-9.20, (3×m, 8 H), 10.10 (s, 2 H).

Compound 8

5,15-bis-(4-{3-[(3-Dimethylamino-propyl)-dimethylammonio]-propyloxy}-phenyl)-porphyrin dichloride

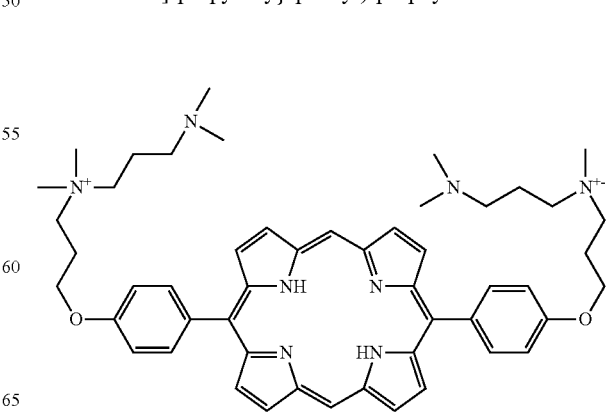

Compound 7 (200 mg, 0.27 mmol) is dissolved in absolute DMF (40 mL) with N,N,N',N'-tetramethyl-1,3-propanediamine (5 mL, 13.9 mmol) and the solution is stirred at 50° C. under argon overnight. After evaporation of the solvent under reduced pressure, the residue obtained is dissolved in methanol (5 mL) and the solution is filtered through a pad of silica gel (depth 2 cm) supported on a steel frit (diameter 3.5 cm). The pad is eluted with methanol (ca. 1 L) followed by acetic acid:methanol:water (3:2:1, by vol.). After evaporation of the solvent from appropriate fractions, the raw product obtained is dissolved in methanol (5 mL) and further purified by chromatography on a column (2.5×40 cm) of Sephadex LH-20 using n-butanol:water:acetic acid (4:5:1, by vol., upper phase) as the developing phase. The first fraction eluted is the desired product. After removal of solvent under reduced pressure the residue obtained is dissolved in methanol (5 mL) and passed through a short column (3.5×20 cm) of anion exchange resin (Amberlite IRA 400, chloride form). After removal of solvent under reduced pressure from the eluate, the residue is treated with diethylether and dried under high vacuum to give the product as a violet solid.

$^1$H-NMR:

$\delta_H$ (300 MHz, CD$_3$OD): 2.20-2.35 (m, 4 H), 2.40-2.50 (m, 4 H), 2.80 (s, 12 H), 3.05 (4 H, t, $^3$J 7.8, 2 H), 3.25 (s, 12 H), 3.45-3.55 (bs, 4 H), 3.65-3.75 (m, 4 H), 4.30 (t, $^3$J 4.2 Hz, 4 H), 7.40, 8.10 (2×d, $^3$J 7.5 Hz, 2×4 H), 8.95, 9.45 (2×d, $^3$J 4.2 Hz, 8 H), 10.40 (s, 2 H).

Compound 9

5,15-bis-[4-(3-Triethylammonio-propyloxy)-phenyl]-porphyrin dichloride

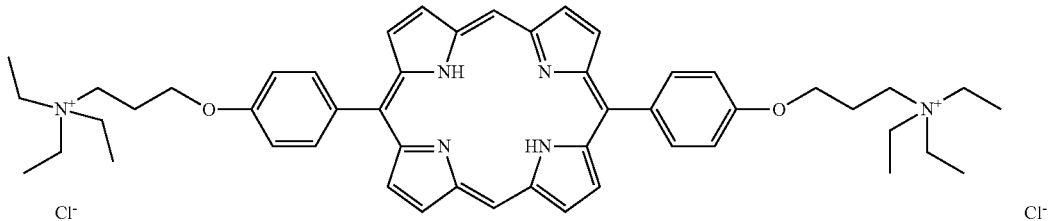 [SMILES: CC[N+](CC)(CC)CCCOc1ccc(-c2c3nc(cc4ccc([nH]4)c(-c4ccc(OCCC[N+](CC)(CC)CC)cc4)c4nc(cc5ccc2[nH]5)C=C4)C=C3)cc1 ; [Cl-] ; [Cl-]]

To a solution of Compound 7 (50 mg, 0.068 mmol) in absolute DMF (20 mL) is added triethylamine (4.7 mL, 0.034 mol, 500 eq.). The mixture is stirred at 60° C. for 24 h. The solvent is removed under reduced pressure and the residue obtained is dissolved in methanol (5 mL) and filtered through a pad of silica gel (depth 2 cm) supported on a steel frit (diameter 3.5 cm). After washing with methanol (ca. 1 L) the pad is eluted with acetic acid:methanol:water (3:2:1, by vol.). After evaporation of the solvent from the eluted fraction, the raw product obtained is dissolved in methanol (5 mL) and purified by chromatography on a column (2.5×40 cm) of Sephadex LH-20 eluting with n-butanol:water:acetic acid (4:5:1, by vol., upper phase). The solvents are removed under reduced pressure from appropriate fractions, the residue obtained is dissolved in methanol (5 mL) and the solution is passed through a short column (3.5×20 cm) of anion exchange resin (Amberlite IRA 400, chloride form) to yield the product as a violet solid after evaporation of solvent.

$^1$H-NMR:

$\delta_H$ (300 Mz, CD$_3$OD): 1.25 (m, 18H), 2.13 (m, 4H), the signals for —CH$_2$NCH$_2$ (16H) are in the area 3.00-3.40 as a part of the multiplet covered by the solvent signals, 4.15 (t, 4H, $^3$J=7.5 Hz), 7.36 (d, 4H, $^3$J=7.5 Hz), 8.15 (d, 4H, $^3$J=7.5 Hz), 9.05 (d, 4H, $^3$J=7.5 Hz), 9.54 (d, 4H, $^3$J=7.5 Hz), 10.45 (s, 2H)

Compound 10

5,15-bis-[4-(3-Trimethylammonio-propyloxy)-phenyl]-porphyrin dichloride

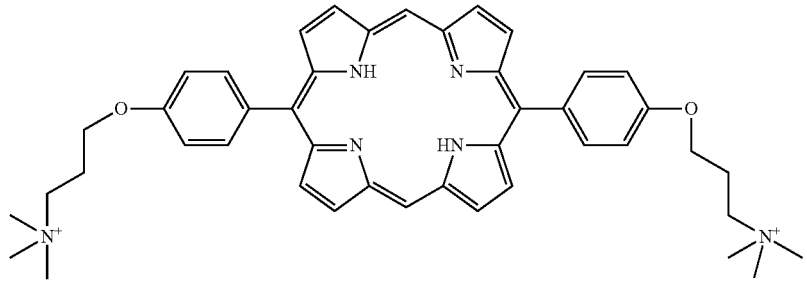

A solution of Compound 7 (300 mg, 0.41 mmol) in absolute DMF (50 mL) is transferred into a 100 mL autoclave. After addition of trimethylamine (4.5 g), the mixture is stirred at 50° C. for 16 h. After evaporation of the solvent, the residue obtained is dissolved in methanol (5 mL) and the solution is filtered through a pad of silica gel (depth 2 cm) supported on a steel frit (diameter 3.5 cm). After washing with methanol (ca. 1 L) the pad is eluted with acetic acid:methanol:water (3:2:1, by vol.). After evaporation of the solvent from appropriate fractions, the residue obtained is dissolved in methanol (5 mL) and purified by chromatography on a column (2.5×40 cm) of Sephadex LH-20, eluting with n-butanol:water:acetic acid (4:5:1, by vol., upper phase). Two fractions are obtained, the first-eluting of which is the desired product. The solvent is removed under reduced pressure and the residue obtained is redissolved in methanol (5 mL) and the solution is passed through a short column (3.5×20 cm) of anion exchange resin (Amberlite IRA 400, chloride form). After evaporation of the solvent under reduced pressure, the residue is treated with methanol:diethylether and dried under high vacuum to give the product as a violet solid.

$^1$H-NMR:

$\delta_H$ (300 Mz, CD$_3$OD): 2.40-2.60 (m, 4 H), 3.30-3.25 (bs, 18 H), 3.75-3.80 (m, 4 H), 4.40 (t, $^3$J 7.5 Hz, 4 H), 7.40, 8.20 (2×d, $^3$J 8.5 Hz, 8 H), 9.05, 9.50 (2×d, $^3$J 4.5 Hz, 8 H), 10.45 (s, 2 H).

Alternative Synthesis Route for Compound 10

Compound 42 (100 mg, 0.2 mMol; see below) is dissolved and potassium carbonate (230 mg 1.7 mMol) is suspended in DMF (30 mL) and to the vigorously-stirred mixture is added a solution of (1-bromopropyl)-trimethylammonium bromide (350 mg, 1.3 mMol) in DMF (5 mL) dropwise at 50° C. during 30 mins. The mixture is heated for 15 h. DMF is removed by rotary evaporation and the residue obtained is dissolved in methanol and the solution is filtered through a pad of silica gel (depth 2 cm) supported on a steel frit (diameter 3.5 cm). After washing with methanol (ca. 1 L) the pad is eluted with acetic acid:methanol:water (3:2:1, by vol.). After evaporation of the solvent from appropriate fractions, the residue obtained is dissolved in methanol (5 mL) and purified by chromatography on a column (2.5×40 cm) of Sephadex LH-20, eluting with n-butanol:water:acetic acid (4:5:1, by vol., upper phase). Two fractions are obtained, the first-eluting of which is the desired product. The solvent is removed under reduced pressure and the residue obtained is redissolved in methanol (5 mL) and the solution is passed through a short column (3.5×20 cm) of anion exchange resin (Amberlite IRA 400, chloride form). After evaporation of the solvent under reduced pressure, the residue is treated with methanol:diethylether and dried under high vacuum to give the product as a violet solid.

Compound 12

5,15-bis-[3-(3-Trimethylammonio-propyloxy)-phenyl]-porphyrin dichloride

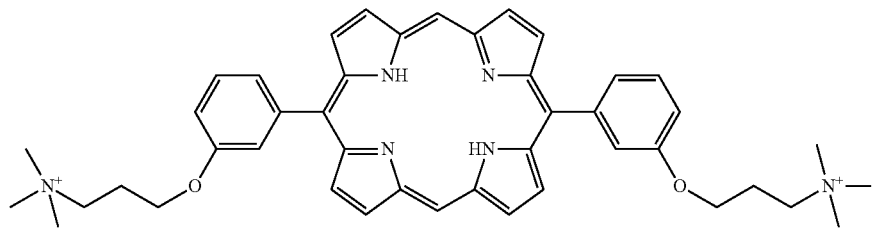

A solution of Compound 11 (400 mg, 0.543 mmol) in DMF (50 mL) is transferred into a 100 mL autoclave. After addition of trimethylamine (6.3 g), the mixture is stirred at 50° C. for 8 h. After evaporation of the solvent under reduced pressure, the residue obtained is dissolved in methanol (5 mL) and the solution is filtered through a pad of silica gel (depth 2 cm) supported on a steel frit (diameter 3.5 cm). After washing the pad with methanol (ca. 1 L), elution with acetic acid:methanol:water (3:2:1, by vol.) affords fractions which, after evaporation of the solvent under reduced pressure, gives a solid residue. This is dissolved in methanol (5 mL) and purified by chromatography on a column (2.5×40 cm) of Sephadex LH-20 eluting with n-butanol:water:acetic acid (4:5:1, by vol., upper phase). Two fractions are eluted from the column, the first of which is the desired product. After removal of the solvent under reduced pressure, the residue obtained is dissolved in methanol (5 mL). The solution is passed through a short column (3.5×20 cm) of anion exchange resin (Amberlite IRA 400, chloride form), the solvent is removed under reduced pressure and the raw product is treated with methanol:diethylether to give a violet solid which is dried under high vacuum.

$^1$H-NMR:

$\delta_H$ (300 Mz, CD$_3$OD): 2.30-2.35 (m, 4 H), 3.15 (s, 18 H), 3.95-4.05 (m, 4 H), 4.20-4.25 (m, 4 H), 7.40-7.45, 7.65-7.70, 7.80-7.85 (3×m, 8 H), 9.00-9.05, 9.40-9.45, (2×m, 8 H), 10.40 (m, 2 H).

Compound 23

5-{-[3-Dimethyl-(3-dimethylaminopropyl)-ammonio-propyloxy]phenyl}-15-(4-dodecyloxy-phenyl)-porphyrin chloride

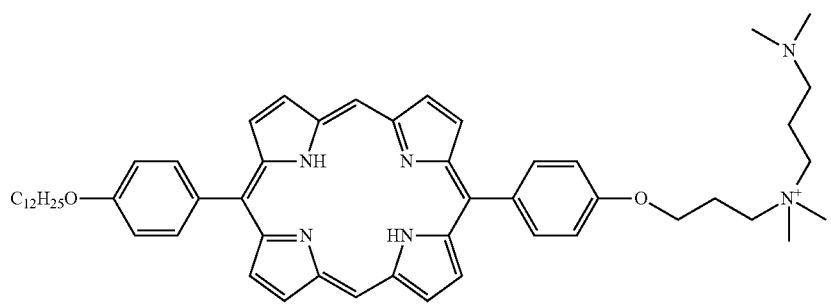

Compound 20 (30 mg, 0.038 mmol) is dissolved with N,N,N',N'-tetramethyl-1,3-propanediamine (156 mg, 1.2 mmol) in THF:DMF (1:1 by vol., 20 mL) and stirred at 50° C. for 18 h. After evaporation of the solvent under reduced pressure, the residue is dissolved in dichloromethane and purified by column chromatography (silica gel Merck 60) eluting with acetic acid:methanol:water (3:2:1, by vol.). After combining appropriate fractions and removal of solvent under reduced pressure, the residue is treatment with dichloromethane:hexane to afford the product as a violet solid.

¹H-NMR:

$\delta_H$ (300 Mz, CDCl$_3$+1% acetic acid): 0.85 (m, 3 H), 1.20-1.40 (m, 18 H), 1.55-1.60 (m, 2 H), 1.60-1.65 (m, 4H), 2.10-2.20 (bs, 8 H), 3.15-3.25 (m, 8 H), 3.75 (bs, 2 H), 4.20 (bs, 2 H), 4.35 (bs, 2 H), 7.15-7.20, 8.10-8.15 (2×m, 8 H), 8.95-9.00, 9.10-9.15, 9.25-9.30 (3×bs, 8 H), 10.20 (s, 2 H).

Compound 25

3-[({3-[(3-{4-[15-(4-Dodecyloxy-phenyl)-porphyrin-5-yl]-phenoxy}-propyl)-dimethyl-ammonio]-propyl}-dimethyl-ammonio)-propyl]-trimethyl-ammonium trichloride

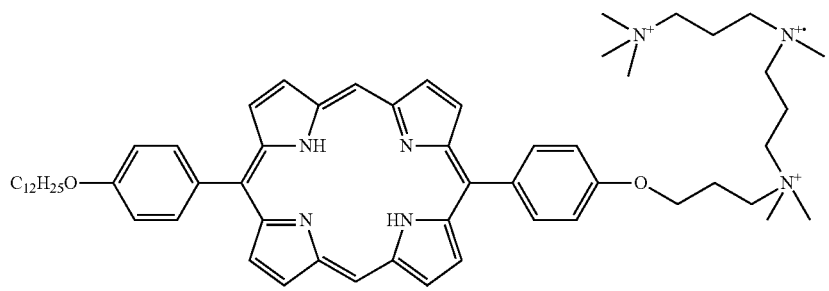

Compound 23 (20 mg, 0.022 mmol) and (1-bromopropyl)-trimethyl-ammonium bromide (26 mg, 0.1 mmol) are dissolved in DMF (15 ml) and stirred overnight at 50° C. After evaporation of the solvent under reduced pressure, the residue is dissolved in methanol (5 ml) and applied to a pad (3 cm deep) of silica gel which is washed with methanol (500 ml) followed by acetic acid:methanol:water (3:2:1 by vol.). After evaporation of the solvent the residue is purified by column chromatography (silica gel Merck 60) using at first acetic acid:methanol:water (3:2:1 by vol.) and then pyridine:acetic acid (1:1 by vol.). The second fraction eluted is collected and dried under vacuum. The residue is dissolved in methanol (2 ml) and purified by chromatography on a column (2.5×40 cm) of Sephadex LH-20 which is eluted with n-butanol:acetic acid:water (5:1:4 by vol., upper phase). After removal of solvent under reduced pressure, the residue is dried under vacuum at 80° C. NMR spectroscopy indicates the product is contaminated with a small proportion of elimination products.

Compound 28

5,15-bis-[3-(3-Trimethylammmonio-propyloxy)-phenyl]-10-undecyl-porphyrin dichloride

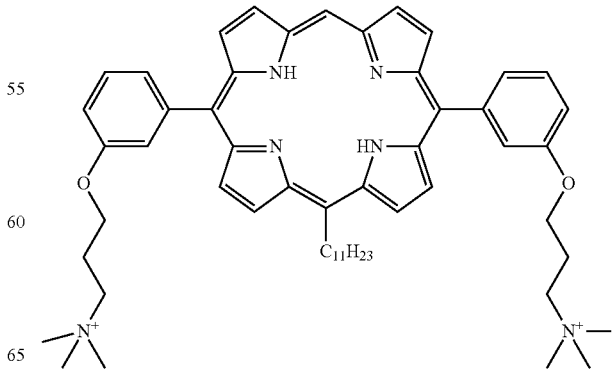

To a solution of Compound 27 (50 mg, 0.08 mmol) in DMF (20 mL) under an argon atmosphere K$_2$CO$_3$ (100 mg, 0.72 mmol) and (3-bromopropyl)-trimethylammonium bromide (300 mg, 1.2 mmol) are added and the mixture is stirred at 50° C. for 18 h. After removal of solvent under high vacuum the residue obtained is dissolved in methanol (5 mL) and filtered through a pad of silica gel (depth 2 cm) supported on a steel frit (diameter 3.5 cm). After washing the pad with methanol (500 mL) it is eluted with acetic acid:methanol:water (3:2:1, v:v). After drying of appropriate combined fractions under high vacuum the residue is dissolved in methanol and purified by column chromatography on Sephadex LH-20 eluting with n-butanol:acetic acid:water (5:1:4, by vol., upper phase). After evaporation of solvent the residue obtained from the first fraction eluted is dissolved in methanol and passed through a short column of anion exchange resin (Amberlite IRA 400, chloride form) to give, after evaporation of solvent, the pure product.

$^1$H-NMR:

$\delta_H$ (300 Mz, CD$_3$OD): 0.85 (t, $^3$J 7.5 Hz, 3 H), 1.20-1.40 (m, 12 H), 1.50 (m, 2 H), 1.80 (m, 2 H), 2.40 (bs, 4 H), 2.55 (m, 2 H), 3.20 (bs, 18 H), 3.65 (bs, 4 H), 4.35 (bs, 4 H), 5.10 (m, 2 H), 7.50-7.55, 7.70-7.85 (2×m, 8 H), 8.95-9.00, 9.25-9.24, 9.50-9.70 (3×bs, 8 H), 10.15 (bs, 1 H).

Compound 31

5-{4-[3-Dimethyl-(3-trimethylammonio-propyl)-ammonio-propyloxy]-phenyl}-15-(4-dodecyloxy-phenyl)-porphyrin dichloride

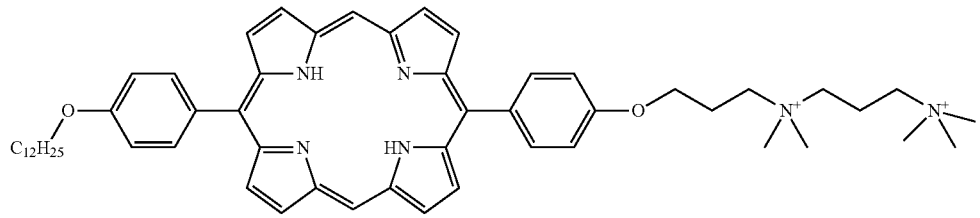

Compound 23 (50 mg, 0.055 mmol) is dissolved with methyl iodide (5 mL, 80 mmol) in absolute DMF (30 mL) and the mixture is stirred at 40° C. for 3 h. After evaporation of solvent the residue obtained is dissolved in methanol (5 mL) and filtered through a pad of silica gel (depth 2 cm) supported on a steel frit (diameter 3.5 cm). After washing the pad with methanol (ca. 1 L) it is eluted with dichloromethane:methanol (2:3 by vol., 500 mL) and then acetic acid:water:methanol (3:1:2, by vol.). After removal of solvent from appropriate pooled fractions the residue obtained is dissolved in acetic acid and purified by column chromatography on Sephadex LH-20 eluting with acetic acid. After evaporation of solvent from appropriate pooled fractions and drying the residue obtained under high vacuum, the residue is dissolved in methanol and passed through a small column (3.5×20 cm) of anion exchange resin (Amberlite IRA 400, chloride form). After evaporation of solvent from the eluate, the product is dried under high vacuum.

Compound 32

5-[4-(3-Dimethyldecyl-ammoniopropyloxy)-phenyl]-15-{4-[3-dimethyl-(3-dimethylaminopropyl)-ammoniopropyloxy]-phenyl}-porphyrin dichloride

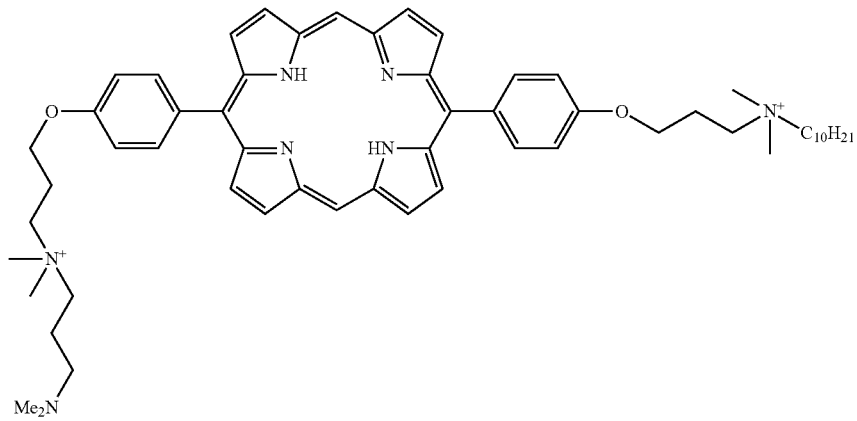

Compound 23 (50 mg, 0.068 mmol) is dissolved with N,N,N',N'-tetramethyl-1,3-propanediamine (354 mg, 1.36 mmol) and N,N-dimethyldecylamine (1 g, 2.72 mmol) in DMF:THF (30 mL, 1:1, by vol.) and the mixture is stirred at 50° C. overnight. After evaporation of the solvent under reduced pressure the residue obtained is dissolved in methanol (10 mL) and filtered through a pad of silica gel (depth 2 cm) supported on a steel frit (diameter 3.5 cm). After washing the pad with methanol (ca. 500 mL) it is eluted with acetic acid:methanol:water (3:2:1, by vol.). The first two fractions eluted are combined and after evaporation of the solvent under reduced pressure the residue obtained is dissolved in methanol and purified by chromatography on a column (2.5× 40 cm) of Sephadex LH-20 eluting with n-butanol:water: acetic acid (4:5:1, by vol.). After removal of solvent under reduced pressure from the second fraction eluted, the residue is dissolved in methanol (5 mL) and passed through a short column (3.5×20 cm) of anion exchange resin (Amberlite IRA 400, chloride form). The eluate is evaporated to dryness and the residue obtained is dried under high vacuum to afford the product.

$^1$H-NMR:

$\delta_H$ (300 MHz, CD$_3$OD): 0.80 (m, 3 H), 1.05-1.25 (m, 10 H), 1.25-1.40 (bs, 2 H), 1.80-1.90 (bs, 4 H), 2.15-2.30 (bs, 2

H), 2.80-3.60 (m, 20 H), 3.80-3.95 (bs, 4 H), 7.05-7.15, 7.85-8.00 (2 ×m, 2×4 H), 8.75-8.90, 9.20-9.35 (2×bs, 2×4 H), 10.15 (bs, 2 H).

Example B

Innate Anti-Bacterial Activity of Compound 10—Determination of Minimum Inhibitory Concentration (MIC) and Minimum Bacteriocidal Concentration (MBC)

The minimum inhibitory concentration (MIC) for an antimicrobial agent against a specific microorganism is defined as the minimum concentration of an antibacterial agent where no apparent visible growth of the organism is observed (FDA definition of Minimum Inhibitory Concentration). MIC's are typically determined using concentrations derived traditionally from serial twofold dilutions (National Committee for Clinical Laboratory Standards (NCCLS) Handbook M7-A5: "Methods for Dilution Antimicrobial Susceptibility Tests for Bacteria that Grow Aerobically; Approved Standard—$5^{th}$ Edition" Volume 20 Number 2. January 2000). The MIC for Compound 10 in the absence of light was investigated, using a protocol based on the MIC protocol produced by the NCCLS (National Committee for Clinical Laboratory Standards (NCCLS) Handbook M7-A5, supra).

The minimum bacteriocidal concentration (MBC) is defined as the minimal concentration of drug needed to kill most (99.9%) of the viable organisms after incubation for a fixed length of time (generally 24 hours) under a given set of conditions (National Committee for Clinical Laboratory Standards (NCCLS) Handbook M26-A; "Methods for determining Bactericidal Activity of Antimicrobial Agents; Approved Guidelines" Volume 19 number 18, September 1999).

Methodology

*Staphylococcus aureus* BAA-44, a multi-drug resistant Methicillin Resistant *Staphylococcus aureus* (MRSA) strain obtained from the ATCC catalogue, was used in this study. The following concentrations of Compound 10 were investigated: 0.764; 0.382; 0.191; 0.0955; 0.0478; 0.0239, 0.0119, 0.00597, 0.00298, 0.00149, 0.00075 & 0.00037 µg/mL. Stock solutions were made up in distilled water and serial dilutions undertaken of this to produce the required concentrations immediately prior to use At least 3 to 5 well-isolated colonies of the same morphological type were selected from an agar plate culture and the growth transferred to a tube containing 100 mL of Isosensitest Broth and the broth culture is incubated at 37° C. overnight. The culture was then be diluted to a final density of $10^4$ cells/mL with fresh Isosensitest Broth and incubated with shaking at 37° C. until the cells entered exponential growth.

0.09 mL of the adjusted inoculum was transferred into each of 24 wells of a polystyrene 96 well microtiter plate. A control well of bacteria alone in the presence of growth medium alone was included (as a positive control).

0.09 mL of the Compound 10 stock solutions from the dilution series were pipetted into the relevant well for the microtiter plates and incubated in the dark at 37° C. and the plates examined after 24 hours incubation to determine the turbidity in each well. These data are used to determine the MIC.

After 24 hours incubation at 37° C., 25 µL samples of the fluid from the wells without visible bacterial growth (four wells up) were inoculated onto nutrient agar plates as spots and incubated at 37° C. for a further 24 hours to determine the MBC.

Results

The results demonstrated that the MIC for Compound 10 in the absence of light was 0.0955 µg/mL, and that the MBC was 0.382 µg/mL (Table 1).

TABLE 1

MIC and MBC data for Compound 10

|  | MIC (µg/mL) | MBC (µg/mL) |
|---|---|---|
| Series 1 | 0.0955 | 0.382* |
| Series 2 | 0.0955 | Not determined |

*growth on sub of 0.191 much reduced from initial inoculum to about $10^3$/ml

CONCLUSIONS

The results demonstrate that in the absence of light Compound 10 has low MIC and MBC values. These data indicate that Compound 10 is considerably more potent as an antibiotic than some traditional antibiotics (see Table 2):

TABLE 2

MIC and MBC values for compound 10 and conventional antibiotics

| Compound | MIC Values (µg/mL) | MBC Values (µg/mL) |
|---|---|---|
| Compound 10 | 0.0955 | 0.382 |
| Vancomycin | $1^a$ | $4$-$16^b$ |
| Zyvox ® (Linezolid) | $4^a$ | $4$->$64^c$ |

[a]Critchley IA et al. Baseline study to determine in vitro activities of daptomycin against gram-positive pathogens isolated in the United States in 2000-2001. *Antimicrobial Agents and Chemotherapy* (2003); 47(5): 1689-93
[b]Biavasco F et al. In vitro antibacterial activity of LY333328, a new semi-synthetic glycopeptide. *Antimicrobial Agents and Chemotherapy* (1997); 41(10): 2165-72
[c]Fuchs PC et al. In vitro bactericidal activity of daptomycin against staphylococci. *Journal of Antimicrobial Chemotherapy* (2002); 49: 467-70

Example C

Innate Anti-Bacterial Activity of Compound 10—Activity Over a Range of Reference Strains and Clinical Isolates The Minimum Inhibitory Concentrations (MIC's) for Compound 10, over a range of reference strains and clinical isolates, were determined using IsoSensitest® broth and Minimum Bactericidal concentrations (MBC's) determined by subculture onto Columbia blood agar.

Methodology

1. A 5 mg/ml stock solution of Compound 10 was made up in water
2. A series of dilutions were undertaken to produce a range of concentrations between 32-0.001 mg/L
3. The test microorganisms were grown up overnight in IsoSensitest® broth
4. The cultures were then diluted with fresh broth to a final concentration of $10^4$ organisms/ml and placed on a shaker for 90 minutes at 37° C.
5. 90 µl of the broth culture containing the microorganisms were transferred to each of 12 wells in a row in a microtitre tray and repeated in a control tray—four organisms per tray.
6. 90 µL of the appropriate Compound 10 dilution was then added to each well containing organisms to give a final dilution series from 16 mg/L to 0.0005 mg/L
7. The solutions were mixed well and incubated in the dark for 24 hours 8. The MIC was recorded and 25 μL from wells showing no growth was subcultured onto blood agar for MBC determination
9. The MBC values were recorded after overnight incubation of the subcultures.
10. Controls of uninoculated broth and broth plus inoculum were undertaken for each organism in each tray Results The results are shown in Table 3.

TABLE 3

MIC and MBC values for compound 10 and conventional antibiotics

| Organism | Strain | Cpd 10 MIC (mg/L) | Cpd 10 MBC (mg/L) |
|---|---|---|---|
| (a) *Staphylococcus aureus* (methicillin resistant) | | | |
| | ATCC BAA-44 Experiment 1 | 0.5 | 0.5 |
| | Experiment 2 | 0.5 | 1 |
| | Experiment 3 | 2 | 2 |
| | Experiment 4 | 0.5 | 1 |
| | Experiment 5 | 0.5 | >1 |
| | Experiment 6 | 0.5 | 1 |
| | NCTC 11939 (EMRSA-1) | 0.5 | 0.5 |
| | EMRSA-15* | 1 | 1 |
| | EMRSA-16* | 0.5 | 0.5 |
| (b) *Staphylococcus aureus* (methicillin sensitive) | | | |
| | NCTC 6571 | 0.5 | 0.5 |
| | ATCC 25923 | 0.5 | 1 |
| (c) *Staphylococcus epidermidis* (methicillin resistant) | | | |
| | 38808* | 0.5 | 0.5 |
| | 33759* | 0.5 | 1 |
| | 33659* | 0.5 | 1 |
| | 36572* | 0.25 | 0.25 |
| (d) *Staphylococcus epidermidis* (methicillin sensitive) | | | |
| | 37453* | 0.5 | 0.5 |
| (e) *Enterococcus faecium* | | | |
| | NCTC 12204 | 1 | 1 |
| | E1* | 0.5 | 1 |
| | E5* | 0.5 | 1 |
| | E19* | 0.5 | 0.5 |
| | E44* | 0.5 | 0.5 |
| (f) *Enterococcus faecalis* | | | |
| | ATCC 29212 | 1 | >1 |
| | E3* | 0.5 | 1 |
| | E4* | 0.5 | 0.5 |
| | E10* | 0.5 | 1 |
| | E37* | 0.5 | 1 |

* = Clinical isolates

CONCLUSIONS

The results demonstrate that Compound 10 has very low MIC and MBC values for a range of gram-positive bacterial strains. The MIC and MBC values are almost identical within the limitations of the methodology, suggesting that the mode of antimicrobial activity is bacteriocidal as opposed to bacteriostatic.

Example D

Toxicity Testing of Compound 10 Against Human Cells

Methodology

Test compounds were screened for toxicity against cultured human skin cells using normal human epidermal keratinocytes (NHEK) and normal human dermal fibroblasts (NHDF), purchased from CellSystems Biotechnologie GmbH, Germany.

The NHEK and NHDF cells were used between passages 3 and 10. The cells were seeded with 7.5 and/or 15×10⁴ cells/well (microtitre plate) and were allowed to attach overnight in an incubator (37° C., 5% $CO_2$). After incubation with different concentrations of the selected photosensitisers for various times, the cells were incubated for 24 hours in the dark.

Toxicity was tested by standard MTT-assay (Mossman et al., 1983 *J. Immunological Methods* 65: 55-63). MTT is an indicator of metabolically active cells. Dependent on enzyme activity in mitochondria a colour reaction can be visualised, which can be measured by ELISA reader (540 nm). The cell viability was normalised to one, which means, the OD values of cells after incubation in the absence of a test compound were normalised to one. Each experiment was repeated three times.

Results

Figure 1:
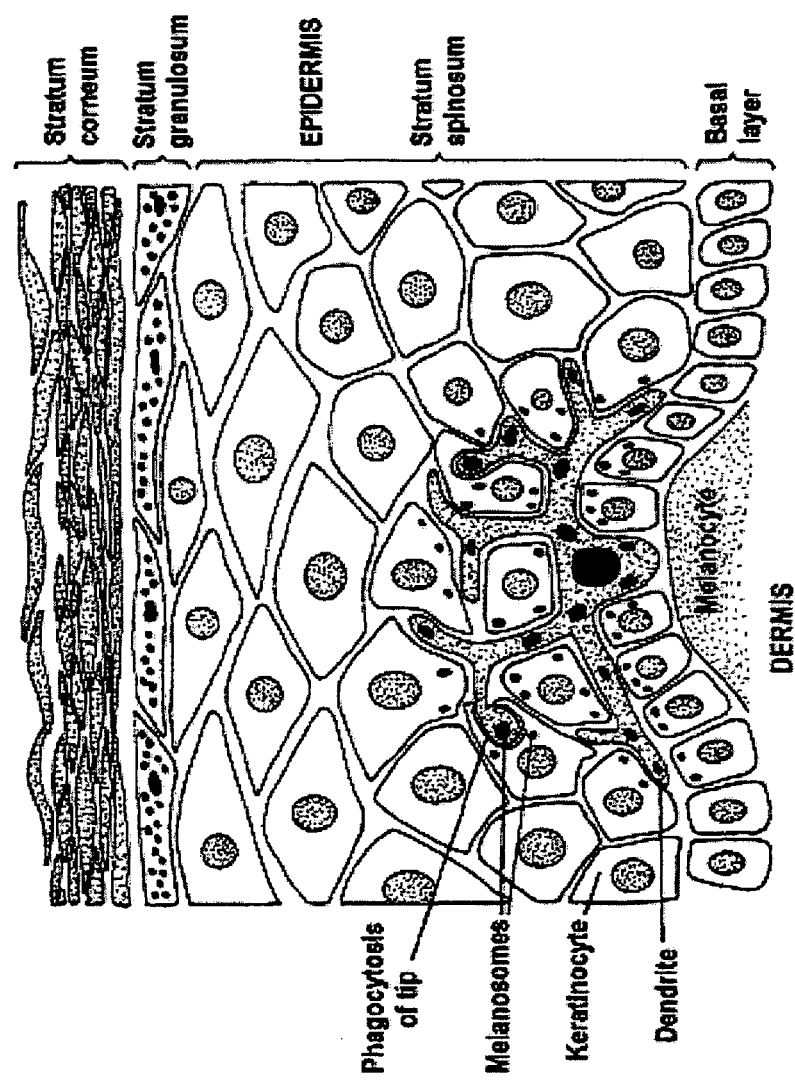
FIG. 1 shows a schematic diagram of the structure of skin.
Figure 2:
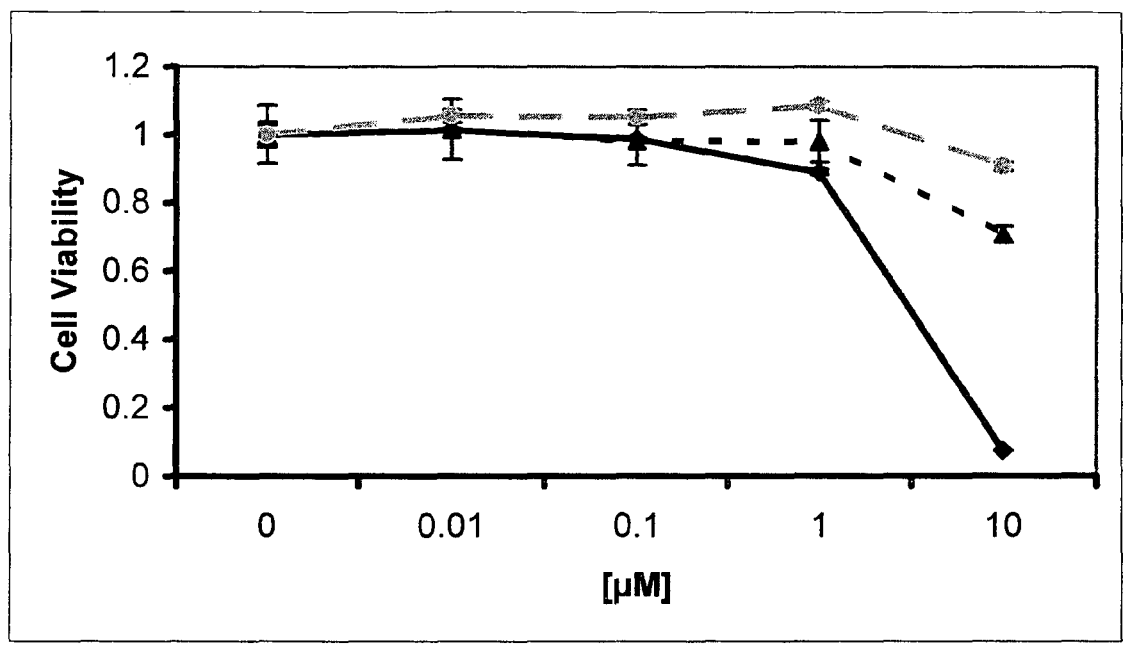
FIG. 2 shows cell toxicity of normal human dermal fibroblasts after 5 minutes, 1 hour and 4 hours incubation with Compound 10.

Results of the toxicity studies in keratinocytes and fibroblasts are shown in FIGS. 2 and 3. The data demonstrate that Compound 10 does not demonstrate an innate toxicity for either normal human epidermal keratinocytes or normal human dermal fibroblasts at doses which are known to have an anti-bacterial effect.

Example E

Binding of Exemplary Compounds with Bacterial Cells

Binding of Compounds 8, 10 and 12 with *E. coli*

*E. coli* cells were incubated for 5 min with Compound 8, 10 or 12 at various concentrations (1-7.5 μM). At the end of the incubation period, the cells were sedimented by centrifugation to remove the fraction of unbound test compound and the cell pellet was resuspended in 2 ml of 2% SDS to obtain cell lysates. After overnight incubation with SDS, the amount of cell-bound test compound was estimated by spectrofluorimetric analysis of the cell lysates. The concentration of the compounds in the cell lysates was calculated by measuring the intensities at the maximum of the emission fluorescence spectrum and interpolating the data on a calibration plot. The amount of cell-bound test compound was expressed as nmoles of compound per mg of cell protein. The protein concentration was determined by the method of Lowry (Lowry et al., 1951, *J. Biol. Chem.* 193:265-275).

All experiments were run in triplicate and the results represent the average of 3 determinations with standard deviations.

The amount of porphyrin recovered from the cells is shown in Table 4.

TABLE 4

| Concentration of compound (μM) | Bound compound (nmoles/mg cell proteins) | | |
|---|---|---|---|
| | Compound 8 | Compound 12 | Compound 10 |
| (a) 0 washings | | | |
| 0.01 | 0.024 ± 0.01 | 0.041 ± 0.02 | 0.026 ± 0.005 |
| 0.1 | 0.056 ± 0.02 | 0.151 ± 0.02 | 0.274 ± 0.05 |
| 0.5 | 0.522 ± 0.2 | 0.806 ± 0.14 | 1.542 ± 0.350 |
| 1 | 3.670 ± 0.7 | 2.70 ± 0.30 | 2.70 ± 0.354 |
| (b) 3 washings | | | |
| 0.01 | 0.009 ± 0.001 | 0.021 ± 0.005 | 0.015 ± 0.0004 |
| 0.1 | 0.030 ± 0.02 | 0.089 ± 0.02 | 0.078 ± 0.02 |

TABLE 4-continued

| Concentration of compound (µM) | Bound compound (nmoles/mg cell proteins) | | |
|---|---|---|---|
| | Compound 8 | Compound 12 | Compound 10 |
| 0.5 | 0.274 ± 0.15 | 0.622 ± 0.10 | 0.334 ± 0.092 |
| 1 | 2.230 ± 0.8 | 1.930 ± 0.20 | 1.278 ± 0.102 |

The results shown in Table 3. show that the three test compounds bind to *E. coli* with similar efficiency and that about 50% of the compound that is associated to the cells at the end of the incubation period (5 min) is removed by 3 washings with PBS.

Example F

Stability Studies

Chemical Stability

The following HPLC methodology was established for the analysis of the exemplary compounds of the invention.

The method involves detection by UV at a wavelength of 420 nm, which is very specific for these compounds. In order to monitor impurities not related to the porphyrin structure (and therefore not absorbing at 420 nm) UV spectra of the whole chromatograms were also recorded between 200 nm and 700 nm by DAD (diode array detector) in certain experiments.

Column: Zorbax Phenyl, 250×4.6 mm, 5 µm
Eluent A: 1.5 g sodium dodecylsulfate+1 mL formic acid in 1000 mL water
Eluent B: 1.5 g sodium dodecylsulfate+1 mL formic acid in 200 mL water+800 mL tetrahydrofurane
Gradient:

| Time [min] | Eluent B [%] |
|---|---|
| 0 | 50 |
| 31 | 65 |
| 32 | 90 |
| 33 | 50 |
| 43 | 50 |

Flow rate: 0.4 mL/min
Detection: 420 nm
Column temperature: 25° C.
Injection volume: 10 µl
Solutions: Porphyrin derivatives were dissolved in eluent A to give a final concentration of approximately 0.3 mg/ml.

Typical retention time of the exemplary compounds was approximately 8 minutes (18 minute runtime).

Qualitative stress tests were undertaken on the exemplary compounds of the invention. Analysis was undertaken by HPLC & LC-MS. The compounds were stress tested in solid form, in an aqueous solution and a solution made up in phosphate-buffered saline buffer. The samples were initially incubated for 7 days at 50° C. and a sample removed for testing. The samples were then incubated for a further 7 days at 70° C., samples removed as before and the samples incubated further for 7 days at 90° C. HPLC analysis of freshly prepared solutions was undertaken and compared to the samples after 7, 14 and 21 days incubation. A visual comparison of the chromatograms was then undertaken and the content of the main products and by-products as area percentage values determined (see FIG. 4).

The 3D plots of the chromatograms show no indications for additional formation of fragments (no signals at lower wavelengths)

The plot in FIG. 5 shows the sample after 21 days in PBS buffer, which showed the largest degradation effect. The results demonstrated minimal degradation on analysis of solid drug and drug in solution heated to 80° C. for a number of weeks.

CONCLUSIONS

Compounds 10 and 12 were both found to exhibit good stability and were very stable even under the stressed conditions of the test protocol. Although Compound 8 was less stable than Compounds 10 and 12, the stability demonstrated was found to be sufficient for practical use.

Stability of Exemplary Compounds in Formulations

The stability of three exemplary compounds (Compounds 8, 10 and 12) and one reference compound (Compound 1), stored at 40° C. in the dark over 8 weeks in polyethylene vials in various aqueous-based formulations, was evaluated as follows:

Sodium laureth sulphate (SLES)+water
9:1 water:ethanol
SLES+9:1 water:ethanol

UV spectra were recorded over the range 350-700 nm over a period of 7 weeks and a visual evaluation of the samples made at 8 weeks.

The results indicate that all compounds tested exhibited good stability over an eight-week period (see FIG. 6).

For Compounds 8 and 10, the stability study was extended to 17 weeks (see FIG. 7).

Example G

Acute Toxicity Testing of Compound 10

Compound 10 was tested at 3.2 mM in a topical formulation in a standard acute dermal toxicity test to determine if any clinical or histological toxicity for the compound could be detected.

The acute toxicity protocol was based on OECD Guidelines for the testing of chemicals/Section 4—Health Effects Test Number 402: Acute Dermal Toxicity.

Results and Conclusions

After clinical, macroscopic and microscopic observation, no clinical toxicology was observed. No histological toxicology of any major organ (including the skin) was observed.

In conclusion, Compound 10 does not result in any acute toxic effect: in fact, no significant clinical or pathological signs related to the substance or its vehicle application were observed.

Example H

Efficacy of Compound 10 Against Biofilms and Slow-Growing Cultures of Staphylococcus Aureus Abstract Background: A key feature of biofilm formation is the bacteria's ability to resist antibiotic activity. The slower growth rate of bacteria in biofilms may be an important factor in increased resistance. We have investigated the activity of Compound 10, the lead compound in an entirely new class of antimicrobial agents, against biofilm and slow growing cultures of *Staphylococcus aureus*.

Methods: MICs were determined for planktonic cultures by broth microdilution according to British Society for Antimicrobial Chemotherapy (BSAC) guidelines. Biofilm MICs (bMIC) and minimum biofilm eradication concentrations (MBECs) were determined using the Calgary biofilm device. The effect of Compound 10 on the viability of cold culture cells was determined by growing S. aureus SH1000 to early exponential phase at 37° C. and resuspending the cells in pre-chilled media, where they were maintained in the presence and absence of Compound 10 and control agents. The effect of Compound 10 on slow growing cells expressing the stringent response was also determined by growing cultures to early log phase and the stringent response induced by the addition of the isoleucyl-tRNA synthetase inhibitor mupirocin. Compound 10 and control agents were then added and samples recovered for viable cell determinations.

Results: Compound 10 had potent antibiofilm activity with a bMIC of 1 µg/mL and a MBEC of 2 µg/mL against S. aureus SH1000, compared with bMICs of 4, 0.5, 0.5 and 0.03 µg/mL and MBECs of >256, >256, >256 and 128 µg/mL for ciprofloxacin, fusidic acid, tetracycline and rifampin respectively. Cold culture and stringent response cultures remained susceptible to Compound 10 with a 5 log drop in viability observed within 1 hour compared with no loss of viability for cultures treated with fosfomycin, vancomycin and daptomycin.

Conclusions: The potent activity of Compound 10 against S. aureus biofilms and slow growing S. aureus cultures demonstrates that its antibacterial activity is independent of the growth state of the bacteria and suggests utility for Compound 10 in the treatment of biofilm-associated S. aureus infections.

Introduction

The formation of biofilms is increasingly recognized as a major factor in a wide range of bacterial infections. Foreign body associated infections, the chronic infection of the lung in cystic fibrosis patients and dental infections are just a few examples of biofilm-mediated infections. In fact, it has recently been reported that 80% of human infections in the developed world are as a direct result of biofilm formation[1].

Furthermore, biofilm cultures are typically highly refractory to eradication with chemotherapy, without developing genotypic resistance. Consequently, the number of therapeutic options is limited and the development of novel antimicrobial agents with antibiofilm activity is increasingly important.

Compound 10 is an example of a new class of antimicrobial agents and represents a new approach to antibacterial therapy. Compound 10 is bactericidal (MBC50 1 µg/mL) and has previously been shown to be active (MIC50 1 µg/mL) against a range of S. aureus strains including methicillin-sensitive S. aureus (MSSA), healthcare-associated methicillin-resistant S. aureus, and community-associated methicillin-resistant S. aureus[2].

The aim of this study was to demonstrate the activity of Compound 10 against biofilm and other slow growing bacterial cultures.

Methods
  Planktonic MICs were determined according to BSAC guidelines[3]
  bMICs and MBECs were determined in a Calgary device according to standard methodologies[4]
  The killing kinetics of Compound 10 against S. aureus SH1000 (MSSA) in cold culture were determined using standard time-kill protocols, with the exceptions that cultures were kept at 4° C.
  The killing kinetics of Compound 10 against stringent cultures of S. aureus SH1000, induced with mupirocin, were determined according to the method of Oliva et al. (2003)[5]

Results
  Compound 10 had antibiofilm activity with a bMIC of 1 µg/mL and a MBEC of 2 µg/mL against S. aureus SH1000 compared with bMICs of 4, 0.5, 0.5, and 0.03 µg/mL and MBECs of >256, >256, >256 and 128 µg/mL for ciprofloxacin, fusidic acid, tetracycline and rifampin respectively (Table 5)
  Cold culture and stringent response cultures remained susceptible to Compound 10, with a 5-log drop in viability observed within 1 hour, compared with no loss of viability for cultures treated with fosfomycin (FIGS. 8 & 9)

TABLE 5

Susceptibility of S. aureus SH1000 biofilms to Compound 10 (XF-73) and control agents

| Drug | MICa (µg/mL) | bMICb (µg/mL) | MBECc (µg/mL) |
| --- | --- | --- | --- |
| Compound 10 | 1 | 1 | 2 |
| Daptomycin | 1 | 2 | >256 |
| Vancomycin | 1 | 2 | >256 |
| Nisin | 2 | 64 | >256 |
| Fosfomycin | 16 | 8 | >256 |
| Fusidic acid | 0.25 | 0.5 | >256 |
| Tetracycline | 1 | 0.5 | >256 |
| Rifampin | 0.008 | 0.02 | >256 |
| Ciprofloxacin | 2 | 4 | >256 |
| Cefotaxime | 0.5 | 4 | >256 |
| Chlorhexidine | 2 | 1 | >256 |
| CTAB[a] | 2 | 2 | >256 |
| Flucloxacillin | 0.125 | 4 | >256 |
| Gentamycin | 0.5 | 1 | >256 |
| Meropenem | 0.5 | 0.5 | >256 |
| Mupirocin | 0.125 | 0.25 | >256 |

CONCLUSIONS

Compound 10 has greater S. aureus anti-biofilm activity when compared with ciprofloxacin, fusidic acid, tetracycline and rifampin Compound 10 remains potently bactericidal against cold culture and stringent response cultures, where the bactericidal activity of other antibacterial agents is significantly reduced These data demonstrate that the bactericidal activity of Compound 10 is independent of the growth state of the bacteria treated The potent S. aureus antibiofilm activity of Compound 10 combined with its retained bactericidal activity against slow growing cultures make it a useful agent for the prevention and treatment of such infections

REFERENCES

1. National Institute of Health [Internet]. [cited 2008 Sep. 17]; Available from http://grants.nih.gov/grants/guide/pa-files/PA-03-047.html
2. Love W G, Rhys-Williams W, Hayter I et al. 2008 ECCMID Barcelona. Abstract P 559.
3. Andrews J M. J Antimicrob Chemother. 2001; 48 (Suppl. S1):5-16.
4. Ceri H, Olson M E, Stremick C, et al. J Clin Microbiol. 1999; 37(6):1771-1776.

5. Oliva B, Miller K, Caggiano N, et al. Antimicrob Agents Chemother. 2003; 47(2):458-466.

Example I

Efficacy of Compound 10 and Compound 12 Against Biofilms and Slow-Growing Cultures of Staphylococcus Aureus The following Example relates to the efficacy of Compound 10 (XF-73) and Compound 12 (XF-70) against biofilms and slow-growing cultures of *S. aureus*, and provides a comparison of those compounds and various control agents.

Effect of XF Drugs on Non-Dividing Staphylococci

During infection bacteria seldom encounter optimal growth conditions and indeed long periods of limited, or arrested, growth are normal in which the organisms enter a quiescent state (Kolter et al, 1993) which may contribute to the creation of persistent bacterial infections (Nataro et al., 2000). *S. aureus* is known to modulate gene expression to withstand sub-optimal growth conditions (Somerville et al., 2002) and it is likely that nondividing bacteria are present in staphylococcal endocarditis and osteomyletis (Mascio et al., 2007). Antimicrobial drugs that are bactericidal under growth-arrested conditions may therefore have clinical advantages over those which do not display such activities (Mascio et al., 2007).

When nutrients become limiting for growth bacteria adjust their metabolism from one that supports growth to one that provides for long survival in the absence of nutrients. In many bacteria a key facilitator of this physiological switch, known as the stringent response, is accumulation of guanosine pyrophosphate and pentaphosphate (Traxler et al., 2008). The antibiotic mupirocin is a strong inducer of the stringent response in *S. aureus* and effectively causes starvation of charged isoleucyl tRNA by potent inhibition of isoleucy ltRNA synthetase (IRS) (Oliva et al., 2003). The activity of XF drugs against *S. aureus* SH1000 prevented from growing by the addition of mupirocin (Oliva et al., 2003), was therefore examined (FIG. 10). As an alternative method for arresting growth, bacteria were suspended in cold growth medium (Mascio et al., 2007) and the bactericidal activity of XF drugs was also determined under these conditions (FIG. 11).

Previous studies have demonstrated that the stringent response completely abolishes the bactericidal activity of fosfomycin, cycloserine, β-lactams and vancomycin against *S. aureus* 8325-4 (Oliva et al., 2003). Fosfomycin was included as a control in the present studies with strain SH1000 (FIG. 10) and the results demonstrate, not unexpectedly, that the bactericidal activity of fosfomycin is completely attenuated under conditions of stringency thereby validating the use of mupirocin as an inducer of the stringent response in strain SH1000. XF-70 and XF-73 retained potent bactericidal activity against non-growing cultures of SH1000 prevented from growth by induction of the stringent response (FIG. 10). Nisin retains some bactericidal activity under stringent conditions but this is not as predominant as that displayed by XF-70 and XF-73 (FIG. 10).

The effect of XF drugs on the viability of cold culture cells was determined by growing *S. aureus* SH1000 to early exponential phase at 37° C., harvesting the cells by centrifugation (5,000×g, 10 min.) and resuspending them in pre-chilled media where they were maintained in the presence and absence of XF drugs and control agents for 5 hours. XF-70 and XF-73 retained potent bactericidal activity against *S. aureus* SH1000 whose growth had been arrested by lowering the temperature to 4° C. (FIG. 11). Under these conditions both daptomycin and nisin retained some bactericidal activity, but the ability of vancomycin to kill the organisms was abolished (FIG. 11).

Activity of XF Drugs Against Biofilms of *S. aureus* SH1000

A biofilm is a community of microbial cells irreversibly associated with a surface and enclosed in a matrix of polysaccharide material secreted by the organisms (Costerton 2001; Donlan, 2002; Hall-Stoodley et al., 2004). Biofilms formed on catheters and other indwelling medical devices by pathogenic Gram-positive bacteria present significant problems in the hospital environment (Costerton 2001; Donlan, 2002; Hall-Stoodley et al., 2004; Toney 2007). Biofilms are notoriously refractory to antibiotic therapy and are generally not subject to elimination by the host immune response. There is a clear need to identify antimicrobial agents with the ability to prevent bacterial biofilm formation, or to eradicate them once formed (Toney 2007). The slower growth rate of bacteria in biofilms may be an important factor in increased resistance to conventional antibiotics. In view of the ability of XF-70 and XF-73 to retain bactericidal activity against non-growing staphylococci (see above) we have also investigated the activity of these drugs against biofilms of *S. aureus* SH1000.

Biofilm MICs and minimum biofilm eradication concentrations (MBEC) were determined in the Calgary Biofilm Device (Nunc Inc, Roskilde, Denmark) as described by Miller et al., 2005. This involves the following steps. Aliquots (200 μL) of exponential phase cultures of strain SH1000 were added to each well of a 96-well microtitre tray. The lid assembly, which has 96 polystyrene pegs corresponding to each well, was then replaced and the system incubated for 24 hours at 37° C. on a rocking platform. Following this a biofilm of approximately $10^7$ cfu matured on each peg. The lid was then washed twice in phosphate-buffered saline (PBS) to remove residual planktonic growth and then placed into a microtitre tray with fresh media containing doubling dilutions of the test antibiotic. The system was then incubated for 24 hours at 37° C. on a rocking platform. The MIC was defined as the lowest concentration of antibiotic completely inhibiting visible growth after this incubation. After the MIC was recorded, the lid assembly was again washed twice in PBS to remove planktonic cells and remaining antibiotic and then placed into fresh drug-free media. The system was incubated for a further 24 hours and the MBEC was defined as the lowest concentration of antibiotic completely inhibiting the re-establishment of planktonic growth.

XF compounds show excellent activity against *S. aureus* SH1000 biofilms compared with many other antimicrobial agents (Table 6). This was reflected in low bMIC values and extended to potent biofilm eradication activity (MBEC), a property not exhibited by the other antimicrobial agents used as controls (Table 6).

TABLE 6

Susceptibility of *S. aureus* SH1000 biofilms to Compound 12 (XF-70), Compound 10 (XF-73) and comparator antibiotics.

| Drug | MIC (μg/ml) | bMIC (μg/ml) | MBEC (μg/ml) |
| --- | --- | --- | --- |
| Ciprofloxacin | 2 | 4 | >256 |
| Fusidic acid | 0.25 | 0.5 | >256 |
| Tetracycline | 1 | 0.5 | >256 |
| Rifampicin | 0.008 | 0.02 | >256 |
| Cpd 12 (XF-70) | 1 | 1 | 2 |
| Cpd 10 (XF-73) | 1 | 1 | 2 |
| Cefotaxime | 0.5 | 4 | >256 |
| Chlorhexidine | 2 | 1 | >256 |
| CTAB[a] | 2 | 2 | >256 |
| Daptomycin | 1 | 2 | >256 |

TABLE 6-continued

Susceptibility of S. aureus SH1000 biofilms to Compound 12 (XF-70), Compound 10 (XF-73) and comparator antibiotics.

| Drug | MIC (µg/ml) | bMIC (µg/ml) | MBEC (µg/ml) |
| --- | --- | --- | --- |
| Flucloxacillin | 0.125 | 4 | >256 |
| Fosfomycin | 16 | 8 | >256 |
| Gentamycin | 0.5 | 1 | >256 |
| Meropenem | 0.5 | 0.5 | >256 |
| Mupirocin | 0.125 | 0.25 | >256 |
| Nisin | 2 | 64 | >256 |
| Vancomycin | 1 | 2 | >256 | bMIC = biofilm MIC,
MBEC = minimum biofilm eradication concentration.

REFERENCES

Costerton, J. W. (2001). Cystic fibrosis pathogenesis and the role of biofilms in persistent infection. Trends in Microbiology 9: 50-52.

Donlan, R. M. (2002). Biofilms: microbial life on surfaces. Emerging Infectious Diseases 8: 881-890.

Hall-Stoodley, L., Costerton, J. W., & Stoodley, P. (2004). Bacterial biofilms: from the natural environment to infectious diseases. Nature Reviews Microbiology 2: 95-108.

Kolter, R. D., Siegele, D. A., & Tormo, A. (1993). The stationary phase of the bacterial life cycle. Annual Review of Microbiology 47: 855-874.

Mascio, C. T. M., Alder, J. D. & Silverman, J. A. (2007). Bactericidal action of daptomycin against stationary-phase and nondividing Staphylococcus aureus cells. Antimicrobial Agents and Chemotherapy 51: 4255-4260.

Nataro, J. P., Blaser, M. J., & Cunningham-Rundles, S. (2000). Persistent bacterial infections: commensalism gone awry or adaptive niche? In, Persistent Bacterial Infections (J. P. Nataro, M. J. Blaser & S. Cunningham-Rundles, eds.), American Society for Microbiology Press, Washington, D.C.

Oliva, B., Miller, K., Caggiano, N., O'Neill, A. J., Cuny, G. D., Hoemann, M. Z., Hauske, J. R. & Chopra, I. (2003). Biological properties of novel antistaphylococcal quinoline-indole agents. Antimicrobial Agents and Chemotherapy 47: 458-466

Somerville, G. A., Chaussee, M. S., Morgan, C. I., Fitzgerald, J. R., Dorward, D. W., Reitzer, L. J. & Musser, J. M. (2002). Staphylococcus aureus aconitase inactivation unexpectedly inhibits exponential-phase growth and enhances stationary-phase survival.

Traxler, M. F., Summers, S. M., Nguyen, H-T., Zacharia, V. M., Hightower, G. A., Smith, J. T., & Conway, T. (2008). The global, ppGpp-mediated stringent response to amino acid starvation in Escherichia coli. Molecular Microbiology 68: 1128-1148.

Toney, J. H. (2007). Biofilms—a neglected antibacterial target? Current Opinion in Investigational Drugs 8: 598-599.

Example J

Efficacy of Compound 10 and Compound 12 Against Slow-Growing Cultures of Staphylococcus Aureus Methods The anti-staphylococcal activities of Compound 10, Compound 12 and a range of comparator agents against slow-growing cultures of Staphylococcus aureus were studied using standard time-kill methodology (Oliva et al. 2003, Hobbs et al. 2008). Staphylococcus aureus SH1000 cultures were grown to early exponential phase ($OD_{600\,nm}$ of 0.2) in Mueller-Hinton broth (MHB) before being exposed to antibacterial agents at 4×MIC. An untreated culture served as the negative control. The experiments were undertaken in triplicate.

Cultures Expressing the Stringent Response

The antibiotic mupirocin is a strong inducer of the stringent response in S. aureus and causes starvation of charged isoleucyl tRNA by potent inhibition of isoleucyl tRNA synthetase (IRS) (Oliva et al. 2003, Cassels et al. 1995) Stringency was induced in SH1000 cultures by adding mupirocin (4 mg/L) to cells in the early exponential growth phase ($OD_{600\,nm}$ of 0.2) (Oliva et al. 2003, Cassels et al. 1995). Cultures were incubated with mupirocin for 30 minutes before sampling began. Cultures were maintained at 37° C., and samples were taken at 30 minute intervals for 300 minutes, serially diluted in phosphate buffered saline (PBS) and diluted culture was spread on Mueller-Hinton agar and was incubated at 37° C. for 18-24 hours before the number of CFU were counted.

Cold Cultures

Cold cultures were prepared by growing SH1000 cells to early exponential phase ($OD_{600\,nm}$ of 0.2) at 37° C. Cultures were then centrifuged and the cell pellet was resuspended in MHB pre-chilled to 4° C. The killing kinetics of antimicrobial agents were studied as described in the section above, with the exception that cultures were maintained at 4° C. over the 5 hour sampling period.

Results

Effects of Compound 10 and Compound 12 on S. aureus Expressing the Stringent Response The activity of Compound 10 and Compound 12 against S. aureus SH1000 that had been prevented from growing by the addition of mupirocin was examined. Previous studies have demonstrated that the stringent response completely abolishes the bactericidal activity of β-lactam antibiotics and fosfomycin against S. aureus (Oliva et al. 2003) Fosfomycin was included as a control in the present studies. At 4×MIC fosfomycin activity was completely attenuated under conditions of stringency (FIG. 12). Similar effects were observed for rifampicin (FIG. 12). In contrast Compound 10 and Compound 12 retained potent bactericidal activity against cultures of SH1000 prevented from growth by induction of the stringent response (FIG. 12).

Effects of Compound 10 and Compound 12 on Cold Cultures

The effect of Compound 10 and Compound 12 on the viability of cold culture cells was determined over a period of 5 hours (FIG. 13). Low temperature had no effect on the activity of Compound 10 and Compound 12 which retained potent bactericidal activity against S. aureus SH1000 whose growth had been arrested by the temperature shift (FIG. 13). Under these conditions both daptomycin and nisin retained limited bactericidal activity, but the ability of other agents to kill the organisms was abolished (FIG. 13).

CONCLUSIONS

Compound 10 and Compound 12 remained highly active against various forms of slow growing or non-dividing S. aureus.

REFERENCES

Cassels R, Oliva B, Knowles D. Occurrence of the regulatory nucleotides ppGpp and pppGpp following induction of the stringent response in staphylococci. J Bacteriol 1995; 177: 5161-65.

Hobbs J K, Miller K, O'Neill A J et al. Consequences of daptomycin mediated membrane damage in *Staphylococcus aureus*. *J Antimicrob Chemother* 2008; 62: 1003-8.

Oliva B, Miller K, Caggiano N, et al. Biological properties of novel antistaphylococcal quinoline-indole agents. *Antimicrob Agents Chemother* 2003 47: 458-466.

Example K

Efficacy of Compound 10 and Compound 12 Against Stationary Phase Cultures of *Staphylococcus Aureus*

Methods

The anti-staphylococcal activities of Compound 10, Compound 12 and a range of comparator agents against stationary phase cultures of *Staphylococcus aureus* were studied using standard time-kill methodology (Oliva et al., 2003, Hobbs et al., 2008). A growth curve was constructed to identify when SH1000 cultures enter and leave stationary phase. 50 mL of Mueller-Hinton broth (MHB) was inoculated with 500 μL of *Staphylococcus aureus* SH1000 overnight culture and was maintained at 37° C. with agitation for 8 days. The culture turbidity at $OD_{600\ nm}$ was measured at regular intervals using a Jenway 6300 spectrophotometer with a 1 cm light path (Jenway, Essex, UK).

*Staphylococcus aureus* SH1000 cultures were grown to early, mid and late stationary phase at 37° C. by incubation for 24, 48 and 72 hours respectively. Cultures were centrifuged, the supernatant was removed, and then a portion of the cell pellet was resuspended in the counterpart supernatant to an $OD_{600\ nm}$ of 0.2 ($10^8$ bacteria/mL). A time-kill assay was then performed on these stationary phase suspensions to study the effects of antimicrobial agents on bacterial cell viability. An untreated culture served as the negative control. The experiments were undertaken in triplicate.

Results

Effects of Compound 10 and Compound 12 on Stationary Phase Cultures of *S. aureus*

The beginning and end of stationary phase were established for *S. aureus* SH1000 cultured in MHB at 37° C. by examining growth curves for the organism over extended periods. Cells were defined as entering stationary phase after 24 hours of growth and exiting at 96 hours, after which culture turbidity declined, indicating bacterial lysis and death. Therefore, early stationary phase was considered to begin 24 hours after inoculation, mid stationary phase at 48 hours and late stationary phase at 72 hours. In order to avoid inoculum effects for susceptibility testing associated with the high cell densities achieved in stationary phase cultures, organisms were recovered at the 24 hour, 48 hour and 72 hour time points and diluted to $10^8$ bacteria/mL in the spent growth medium from these cultures prior to determination of the bactericidal activities of inhibitors.

Compound 10 and Compound 12 retained potent bactericidal activity against cells recovered from all time points in the stationary phase (FIGS. 14-16). In contrast to Compound 10 and Compound 12 the activity of comparator agents against stationary phase cultures was poor (FIGS. 14-16).

CONCLUSIONS

Compound 10 and Compound 12 remained highly active against cultures of *S. aureus* in early, mid and late stage of stationary phase.

REFERENCES

Hobbs J K, Miller K, O'Neill A J et al. Consequences of daptomycin mediated membrane damage in *Staphylococcus aureus*. *J Antimicrob Chemother* 2008; 62: 1003-8.

Oliva B, Miller K, Caggiano N, et al. Biological properties of novel antistaphylococcal quinoline-indole agents. *Antimicrob Agents Chemother* 2003 47: 458-466.

The invention claimed is:

1. A method for killing or inhibiting the growth of a microbial biofilm within the body of a patient in the absence of irradiation with a photodynamic light source or an ultrasound source, wherein said microbial biofilm is not associated with atopic dermatitis, the method comprising administering to the patient a compound of formula I or II in the absence of irradiation with a photodynamic light source or an ultrasound source,

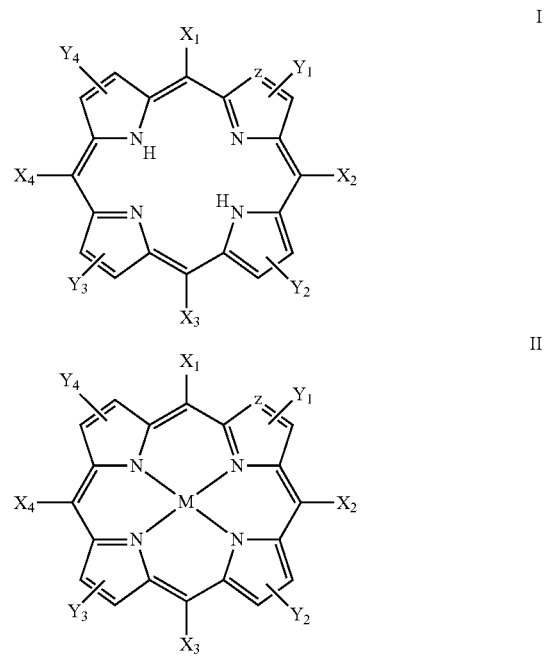

wherein:

$X_1$, $X_2$, $X_3$ and $X_4$ independently represent a hydrogen atom, a lipophilic moiety, a phenyl group, a lower alkyl, alkaryl or aralkyl group, or a cationic group of the following formula;

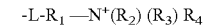

wherein:

L is a linking moiety or is absent;

$R_1$ represents lower alkylene, lower alkenylene or lower alkynylene, which is optionally substituted by one or more substituents selected from lower alkyl, lower alkylene (optionally interrupted with oxygen), fluoro, $OR_5$, $C(O)R_6$, $C(O)OR_7$, $C(O)NR_8R_9$, $NR_{10}R_{11}$ and $N^+R_{12}R_{13}R_{14}$; and $R_2$, $R_3$ and $R_4$ independently represent H, aryl, lower alkyl, lower alkenyl or lower alkynyl, the latter three of which are optionally substituted by one or more substituents selected from lower alkyl, lower alkylene (optionally interrupted with oxygen), aryl, $OR_5$, $C(O)R_6$, $C(O)OR_7$, $C(O)$ $NR_8$ $R_9$, $NR_{10}R_{11}$ and $N^+R_{12}R_{13}R_{14}$;

Z is —CH or N; and $Y_1$, $Y_2$, $Y_3$ and $Y_4$ are absent or independently represent aryl, lower alkyl, lower alkenyl or lower alkynyl, the latter three of which are optionally substituted by one or more substituents selected from lower alkyl, lower alkylene (optionally interrupted with oxygen), aryl, OR$_5$, C(O)R$_6$, C(O)OR$_7$, C(O)NR$_8$ R$_9$, NR$_{10}$R$_{11}$, N$^+$R$_{12}$R$_{13}$R$_{14}$, or, taken in conjunction to the pyrrole ring to which they attach, forms a cyclic group;

R$_5$, R$_6$, R$_7$, R$_8$, R$_9$, R$_{10}$, R$_{11}$, R$_{12}$, R$_{13}$ and R$_{14}$ independently represent H or lower alkyl; and M is a metallic element or a metalloid element, provided that at least one of X$_1$, X$_2$, X$_3$ and X$_4$ is a cationic group as defined above and at least one of X$_1$, X$_2$, X$_3$ and X$_4$ is a hydrogen atom.

2. The method according to claim 1 wherein R$_1$ is an unsubstituted lower alkylene, lower alkenylene or lower alkynylene group.

3. The method according to claim 1 wherein R$_2$, R$_3$ and/or R$_4$ are unsubstituted lower alkyl groups.

4. The method according to claim 1 wherein X$_1$, X$_2$, X$_3$ and/or X$_4$ are

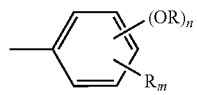

wherein each R independently is —R$_1$—N$^+$(R$_2$) (R$_3$)R$_4$, as defined in claim 1 and 'n' and 'm' are integers between 0 and 3 and wherein the sum of 'n' and 'm' is an integer between 1 and 3.

5. The method according to claim 1 wherein X$_1$ and X$_2$ are hydrogen and X$_3$ and X$_4$ are cationic groups, or X$_2$ and X$_3$ are hydrogen and X$_4$ and X$_1$ are cationic groups.

6. The method according to claim 1 wherein the compound is selected from the group consisting of 5,15-bis-(4-{3-[(3-Dimethylamino-propyl)-dimethyl-ammonio]-propyl-oxyl-phenyl)-porphyrin, 5,15-bis-[4-(3-Triethylammonio-propyloxy)-phenyl]-porphyrin, 5,15-bis-[3-(3-Trimethylammonio-propyloxy)-phenyl]-porphyrin, 5,15-bis-[4-(3-Trimethylammonio-propyloxy)-phenyl]-porphyrin, 5-[3,5-bis-(3-Trimethylammonio-propyloxy)-phenyl]-15-undecyl-porphyrin, 5-{4-[3-Dimethyl-(3-dimethylaminopropyl)-ammonio-propyl-oxy]-phenyl}-15-(4-dodecyloxy-phenyl)-porphyrin, 3-[({3-[(3-{4-[15-(4-Dodecyloxy-phenyl)-porphyrin-5-yl]-phenoxyl -propyl)-dimethyl -ammoniol-propyll-dimethyl-ammonio)-propyl]-trimethyl -ammonium, 5,15-bis-[3-(3-Trimethylammmonio-propyloxy) -phenyl]-10-undecyl-porphyrin, 5-{4-[3-Dimethyl-(3-trimethylammonio-propyl)-ammonio-propyloxy]-phenyl}-15-(4-dodecyloxy-phenyl)-porphyrin, 5-[4-(3-Dimethyldecyl-ammoniopropyloxy) -phenyl]-15-{4-[3-di-methyl-(3-dimethylaminopropyl)-ammoniopropyloxy]-phenyl}-porphyrin, and salts thereof.

7. The method according to claim 6 wherein the compound is 5,15-bis-[4-(3-Trimethylammonio-propyloxy) -phenyl]-porphyrin ("XF-73") or 5,15-bis-[3-(3-Trimethylammonio-propyloxy)-phenyl]-porphyrin ("XF-70"), or a dichloride salt thereof.

8. The method according to claim 6 wherein the compound comprises a central metal ion.

9. The method according to claim 1 wherein the microbial biofilm comprises bacteria.

10. The method according to claim 1 wherein the biofilm is in the oral cavity, urinary tract, sinuses, ear, heart, prostate, bone, lungs, or kidneys.

11. The method according to claim 1 wherein the biofilm is attached to an inert support within the body.

12. The method according to claim 1 wherein the compound is administered orally.

13. The method according to claim 1 wherein the compound is administered parenterally.

14. The method according to claim 1 wherein the compound is administered topically.

15. The method according to claim 1 wherein the patient has a catheter, a stent, a shunt, an intubating or tracheotomy tube, an opthalmic device, a joint prosthesis, an artificial heart valve and/or a breast implant.

16. An in vitro method for killing or inhibiting the growth of a microbial biofilm in the absence of irradiation with a photodynamic light source or an ultrasound source comprising contacting the biofilm in the absence of irradiation with a photodynamic light source or an ultrasound source with a compound of formula I or II of claim 1.

17. A method according to claim 16 wherein the biofilm is in a domestic, commercial or industrial environment.

18. A method for treating a patient suffering from a disease or condition associated with a microbial biofilm in the absence of irradiation with a photodynamic light source or an ultrasound source, wherein said microbial biofilm is not associated with atopic dermatitis, the method comprising administering to the patient a compound of formula I or II of claim 1 in the absence of irradiation with a photodynamic light source or an ultrasound source.

* * * * *